United States Patent
He et al.

(10) Patent No.: US 12,262,123 B2
(45) Date of Patent: Mar. 25, 2025

(54) APPARATUSES, SYSTEMS, AND METHODS FOR MANAGING AUTO-EXPOSURE OF IMAGE FRAMES DEPICTING COLOR-BIASED CONTENT

(71) Applicant: Intuitive Surgical Operations, Inc., Sunnyvale, CA (US)

(72) Inventors: Zhen He, Cupertino, CA (US); Jeffrey M. DiCarlo, Austin, TX (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 37 days.

(21) Appl. No.: 18/014,464

(22) PCT Filed: Jul. 7, 2021

(86) PCT No.: PCT/US2021/040708
§ 371 (c)(1),
(2) Date: Jan. 4, 2023

(87) PCT Pub. No.: WO2022/011027
PCT Pub. Date: Jan. 13, 2022

(65) Prior Publication Data
US 2023/0262347 A1    Aug. 17, 2023

Related U.S. Application Data

(60) Provisional application No. 63/050,583, filed on Jul. 10, 2020.

(51) Int. Cl.
*H04N 23/74* (2023.01)
*A61B 1/00* (2006.01)
(Continued)

(52) U.S. Cl.
CPC ....... *H04N 23/74* (2023.01); *A61B 1/000095* (2022.02); *A61B 1/045* (2013.01);
(Continued)

(58) Field of Classification Search
None
See application file for complete search history.

(56) References Cited

U.S. PATENT DOCUMENTS

| 9,313,415 B2 | 4/2016 | Schieltz | |
| 2007/0182845 A1* | 8/2007 | Hunter | H04N 23/73 348/E5.037 |

(Continued)

OTHER PUBLICATIONS

International Preliminary Report on Patentability for Application No. PCT/US2021/040708 mailed Jan. 19, 2023, 11 pages.
International Search Report and Written Opinion for International Application PCT/US2021/040708 dated Oct. 22, 2021, 14 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Eileen M Adams

(57) ABSTRACT

An illustrative apparatus may determine a color-skew metric for an image frame captured by an image capture system. The color-skew metric may be indicative of an extent to which the image frame skews to a particular color. Based on the color-skew metric and an adaptive target control function, the apparatus may determine a frame auto-exposure target. Based on the frame auto-exposure target, the apparatus may update one or more auto-exposure parameters for use by the image capture system to capture an additional image frame. Corresponding apparatuses, systems, and methods for managing auto-exposure of image frames are also disclosed.

20 Claims, 13 Drawing Sheets

(51) Int. Cl.
  *A61B 1/045*   (2006.01)
  *A61B 1/06*   (2006.01)
  *H04N 9/78*   (2006.01)
  *H04N 23/50*   (2023.01)
  *H04N 23/71*   (2023.01)
  *H04N 23/72*   (2023.01)
  *H04N 23/73*   (2023.01)
  *H04N 23/76*   (2023.01)
  *H04N 23/86*   (2023.01)

(52) U.S. Cl.
  CPC ............. *A61B 1/0655* (2022.02); *H04N 9/78* (2013.01); *H04N 23/555* (2023.01); *H04N 23/71* (2023.01); *H04N 23/72* (2023.01); *H04N 23/73* (2023.01); *H04N 23/76* (2023.01); *H04N 23/86* (2023.01)

(56) References Cited

U.S. PATENT DOCUMENTS

| | | | |
|---|---|---|---|
| 2012/0067956 A1* | 3/2012 | Gao | G06K 7/10792 |
| | | | 235/455 |
| 2014/0052004 A1 | 2/2014 | D'Alfonso et al. | |
| 2016/0093029 A1* | 3/2016 | Micovic | G06T 3/14 |
| | | | 348/229.1 |
| 2019/0335150 A1* | 10/2019 | Shin | G06T 7/90 |
| 2020/0351524 A1* | 11/2020 | Lee | H04N 19/182 |
| 2021/0007810 A1* | 1/2021 | Rainis | A61B 34/20 |
| 2021/0110190 A1 | 4/2021 | Park et al. | |
| 2021/0150963 A1* | 5/2021 | Yang | G09G 3/2003 |

\* cited by examiner

APPARATUSES, SYSTEMS, AND METHODS FOR MANAGING AUTO-EXPOSURE OF IMAGE FRAMES DEPICTING COLOR-BIASED CONTENT

RELATED APPLICATIONS

The present application is a U.S. National Stage Application under 35 U.S.C. § 371 of International Application No. PCT/US2021/040708, filed on Jul. 7, 2021, which claims priority to U.S. Provisional Patent Application No. 63/050,583, filed Jul. 10, 2020, the contents of which are hereby incorporated by reference in their entirety.

BACKGROUND INFORMATION

Auto-exposure algorithms operate by analyzing image frames to determine how much light is present at a scene depicted by the image frames and by updating, based on this analysis, auto-exposure parameters of an image capture device capturing the image frames. In this manner, the auto-exposure parameters may be continuously updated to cause the image capture device to provide a desired amount of exposure for image frames being captured. Without good auto-exposure management, detail may be lost during the image capture process by either over-exposure (e.g., where details are lost because of saturation and the image looks too bright) or under-exposure (e.g., where details are lost because of noise and the image looking too dark).

While conventional auto-exposure algorithms adequately serve many types of images, images depicting color-biased content (e.g., content that skews toward one part of the color spectrum instead of having a balance of many colors) may present particular challenges. For example, certain colors are naturally associated with less luminance than other colors, thereby making the colors look dark. When conventional auto-exposure algorithms process image frames that depict such color-biased content, the algorithms may overexpose or underexpose the image frames and/or encounter other undesirable issues.

SUMMARY

The following description presents a simplified summary of one or more aspects of the apparatuses, systems, and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An illustrative apparatus for managing auto-exposure of image frames may include one or more processors and memory storing executable instructions that, when executed by the one or more processors, cause the apparatus to perform various operations described herein. For example, the apparatus may determine a color-skew metric for an image frame captured by an image capture system. The color-skew metric may be indicative of an extent to which the image frame skews to a particular color. Based on the color-skew metric and an adaptive target control function, the apparatus may determine a frame auto-exposure target, Based on the frame auto-exposure target, the apparatus may update one or more auto-exposure parameters for use by the image capture system to capture an additional image frame.

An illustrative system for managing auto-exposure of image frames may include an illumination source, an image capture device, and one or more processors. The illumination source may be configured to illuminate tissue within a body during a medical procedure. The image capture device may be configured to capture an image frame sequence during the medical procedure. The image frame sequence may include an image frame depicting an internal view of the body that features the tissue illuminated by the illumination source. The one or more processors may be configured to determine a color-skew metric for the image frame. The color-skew metric may be indicative of an extent to which the image frame skews to a red color. Based on the color-skew metric and an adaptive target control function, the one or more processors may determine a frame auto-exposure target, Based on the frame auto-exposure target, the one or more processors may update one or more auto-exposure parameters for use by the image capture device or the illumination source in capturing an additional image frame of the image frame sequence.

An illustrative non-transitory computer-readable medium may store instructions that, when executed, cause one or more processors of a computing device to perform various operations described herein. For example, the one or more processors may determine a color-skew metric for an image frame captured by an image capture system. The color-skew metric may be indicative of an extent to which the image frame skews to a particular color. The one or more processors may also determine an output of an adaptive target control function given an input of the color-skew metric. Based on the output of the adaptive target control function, the one or more processors may update one or more auto-exposure parameters for use by the image capture system to capture an additional image frame.

An illustrative method for managing auto-exposure of image frames may include various operations described herein, each of which may be performed by a computing device such as an auto-exposure management apparatus described herein. For example, the method may include determining a color-skew metric for an image frame captured by an image capture system. The color-skew metric may be indicative of an extent to which the image frame skews to a particular color. The method may further include determining a frame auto-exposure target based on the color-skew metric and determining a frame auto-exposure value. The method may further include updating, based on the frame auto-exposure target and the frame auto-exposure value, one or more auto-exposure parameters for use by the image capture system to capture an additional image frame.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
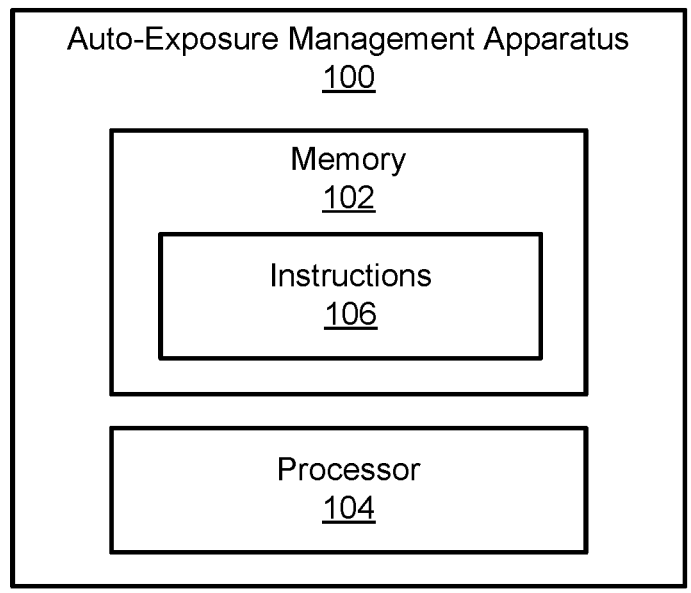
FIG. 1 shows an illustrative auto-exposure management apparatus for managing auto-exposure of image frames according to principles described herein.

Apparatuses, systems, and methods for managing auto-exposure of image frames are described herein. As mentioned above, auto-exposure management of image frames depicting color-biased content may present unique challenges not presented when image frames depict content that is more balanced across the color spectrum. For example, if an image frame is skewed toward a particular color that is associated with less luminance than other colors, and auto-exposure management does not properly take that skew into account, an overly high auto-exposure target may be identified. This may result in subsequent image frames being overexposed. For example, an auto-exposure algorithm may attempt to brighten up images that look dark by virtue of their skewed chrominance toward a naturally dark-looking color and not by virtue of inadequate illumination of the scene. As this occurs, it is possible that an auto-exposure algorithm will saturate a channel associated with the particular color to which the image frame is skewed, thereby introducing color inaccuracies to subsequent image frames along with lost detail resulting from the overexposure. For example, if the color to which an image frame skews is red and the red channel saturates as an auto-exposure algorithm overexposes subsequent image frames, the red in those subsequent image frames may appear to have an orange tone that is not true to the imagery being captured.

As one example of where this type of issue may come into play, an endoscopic image capture device capturing an internal view of a body during a medical procedure on the body (e.g., a surgical procedure, etc.) will be considered. Due to blood and bloody tissue that is pervasive within the body, the image capture device in such a scenario may capture image frames that skew toward a red color (e.g., a color associated with blood depicted in the internal view). Because the red color can be associated with low luminance (e.g., red looks darker than other colors even when exposed to and/or reflecting the same amount of light as the other colors), such image frames may be prone to the overexposure and red saturation issues described above (e.g., making the blood appear slightly orange in some examples).

Apparatuses, systems, and methods described herein provide auto-exposure management to address these and other issues for images that depict color-biased content (e.g., imagery that skews toward one color such as red). For example, auto-exposure management described herein may evaluate, quantify, and otherwise determine the color skew of an image frame (e.g., the extent or degree to which the image frame skews toward a particular color), and may account for this color skew in the determination of an auto-exposure target (e.g., a brightness that the auto-exposure algorithm targets for subsequent image frames). In this way, the auto-exposure management may avoid overcompensating for the potentially misleading luminance associated with certain colors (e.g., the fact that red looks darker than other colors), and avoids the overexposure, underexposure, and/or channel saturation that may result as a consequence of such overcompensation.

Medical procedure examples involving endoscopic views of bloody internals of bodies such as those introduced above will be referred to throughout this description to illustrate various aspects of the claimed subject matter. However, it will be understood that endoscopic images of bloody (and therefore heavily red-skewed) scenes are only intended as examples, and the principles described herein may be applied, in various implementations, to any suitable types of color-skewed content as may serve a particular application or use case. As a few additional examples, for instance, auto-exposure management described herein may find application in capturing closeup images of red objects, capturing scenes in rooms that are painted red, capturing certain landscapes (e.g., sunsets, red leaves in the fall, etc.). Moreover, the principles described herein may apply to various color-biased images and scenarios with colors other than red (e.g., blue, yellow, violet, etc.) whose chrominance properties may similarly cause these colors to naturally appear more or less luminescent than may be accounted for by conventional auto-exposure algorithms.

Various specific embodiments will now be described in detail with reference to the figures. It will be understood that the specific embodiments described below are provided as non-limiting examples of how various novel and inventive principles may be applied in various situations. Additionally, it will be understood that other examples not explicitly described herein may also be captured by the scope of the claims set forth below. Auto-exposure management apparatuses, systems, and methods described herein may provide any of the benefits mentioned above, as well as various additional and/or alternative benefits that will be described and/or made apparent below.

FIG. 1 shows an illustrative auto-exposure management apparatus 100 (apparatus 100) for managing auto-exposure of image frames according to principles described herein. Apparatus 100 may be implemented by computer resources (e.g., servers, processors, memory devices, storage devices, etc.) included within an image capture system (e.g., an endoscopic image capture system, etc.), by computer resources of a computing system associated with an image capture system (e.g., communicatively coupled to the image capture system), and/or by any other suitable computing resources as may serve a particular implementation.

As shown, apparatus 100 may include, without limitation, a memory 102 and a processor 104 selectively and communicatively coupled to one another. Memory 102 and processor 104 may each include or be implemented by computer hardware that is configured to store and/or process computer software. Various other components of computer hardware and/or software not explicitly shown in FIG. 1 may also be included within apparatus 100. In some examples, memory 102 and processor 104 may be distributed between multiple devices and/or multiple locations as may serve a particular implementation.

Memory 102 may store and/or otherwise maintain executable data used by processor 104 to perform any of the functionality described herein. For example, memory 102 may store instructions 106 that may be executed by processor 104. Memory 102 may be implemented by one or more memory or storage devices, including any memory or storage devices described herein, that are configured to store data in a transitory or non-transitory manner. Instructions 106 may be executed by processor 104 to cause apparatus 100 to perform any of the functionality described herein. Instructions 106 may be implemented by any suitable application, software, code, and/or other executable data instance. Additionally, memory 102 may also maintain any other data accessed, managed, used, and/or transmitted by processor 104 in a particular implementation.

Processor 104 may be implemented by one or more computer processing devices, including general purpose processors (e.g., central processing units (CPUs), graphics processing units (GPUs), microprocessors, etc.), special purpose processors (e.g., application specific integrated circuits (ASICs), field-programmable gate arrays (FPGAs), etc.), image signal processors, or the like. Using processor 104 (e.g., when processor 104 is directed to perform operations represented by instructions 106 stored in memory 102), apparatus 100 may perform various functions associated with managing auto-exposure of image frames depicting color-biased content (e.g., content that skews to a particular color such as the blood red color to which endoscopic images of body internals are typically skewed).

Figure 2:
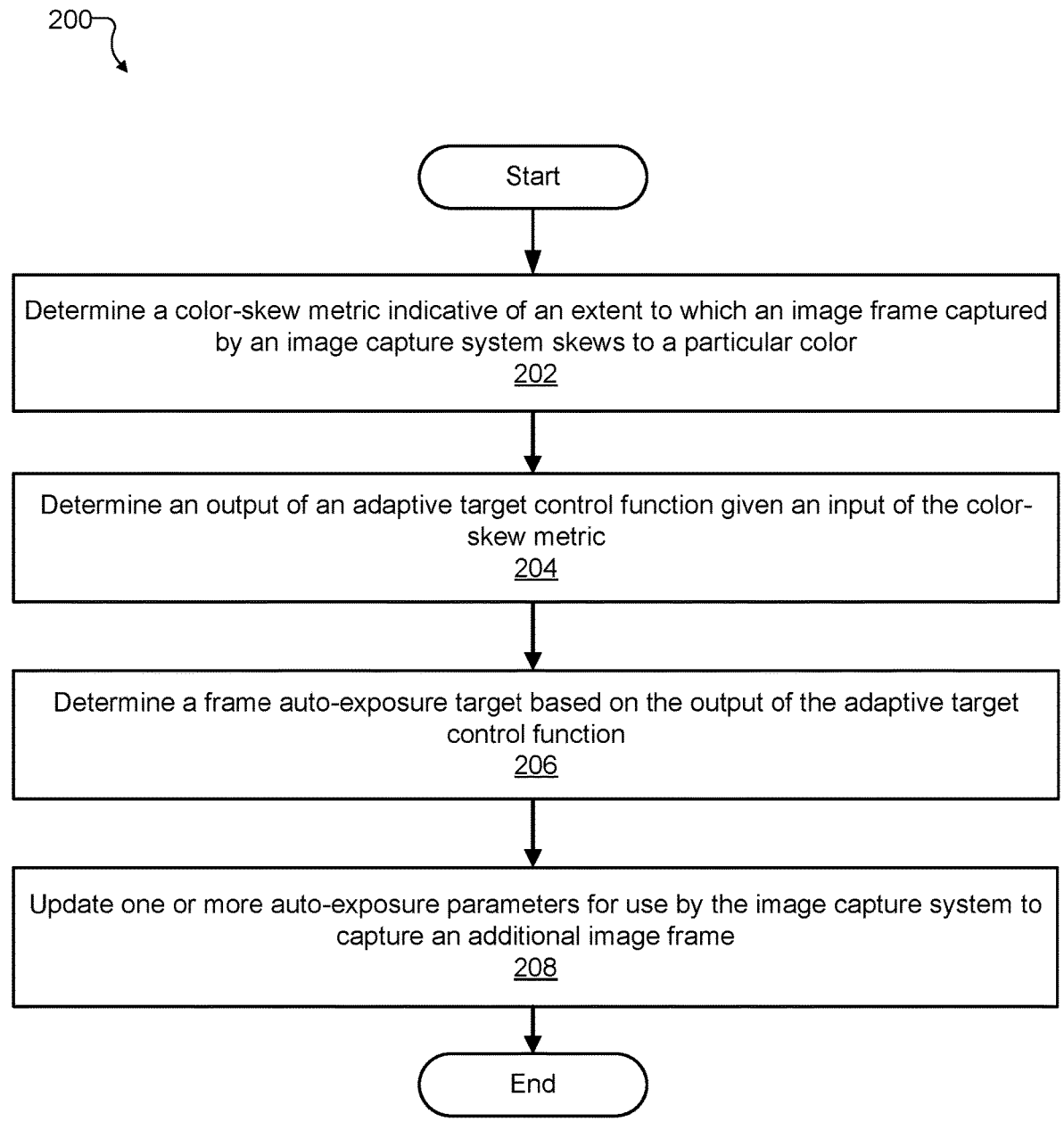
FIG. 2 shows an illustrative auto-exposure management method for managing auto-exposure of image frames according to principles described herein.

FIG. 2 shows an illustrative auto-exposure management method 200 (method 200) that apparatus 100 may perform to manage auto-exposure of image frames in accordance with principles described herein. While FIG. 2 shows illustrative operations according to one embodiment, other embodiments may omit, add to, reorder, and/or modify any of the operations shown in FIG. 2. In some examples, multiple operations shown in FIG. 2 may be performed concurrently (e.g., in parallel) with one another, rather than being performed sequentially as illustrated. One or more of the operations shown in FIG. 2 may be performed by an auto-exposure management apparatus (e.g., apparatus 100), an auto-exposure management system (e.g., an implementation of an auto-exposure management system described below), and/or any implementation thereof.

At operation 202, apparatus 100 may determine a color-skew metric for an image frame captured by an image capture system. The color-skew metric may be indicative of an extent to which the image frame skews to a particular color. For example, in the medical procedure example in which the image frame depicts an internal endoscopic view of a body undergoing the medical procedure, the color-skew metric determined at operation 202 may be implemented as a redness metric that indicative of an extent to which the image frame skews to the red color of the blood and bloody tissue depicted in the image frame. The color-skew metric determined at operation 202 may be determined in any of the ways described herein (e.g., including in accordance with techniques that will be described in more detail below) and may be represented in any manner as may serve a particular implementation. For example, the color-skew metric may be represented as a percentage that vanes between 0% (e.g., for a completely neutral image frame that does not skew to any particular color more than any other) to 100% (e.g., for an image frame that is completely skewed to the particular color). In this example, negative percentages could be used to represent color bias that skews to colors other than the particular color, or this could be accounted for in another way. In other implementations, other representations could be used to quantify the color-skew metric such as a floating-point representation (e.g., a metric that varies between 0.00 and 1.00 or between −1.00 and 1.00, etc.) an integer representation (e.g., a metric that varies between 0 and 5, between 0 and 500, between −10 and 10, etc.), or another suitable representation.

At operation 204, apparatus 100 may determine an output of an adaptive target control function given an input of the color-skew metric determined at operation 202. For example, as will be described and illustrated in more detail below, the adaptive target control function may define how image frames having different color-skew metrics are to be analyzed in terms of the auto-exposure data points (e.g., auto-exposure targets, auto-exposure values, etc.) that are determined for the image frames. A particular adaptive target control function, for instance, may define a threshold that, if not exceeded by a color-skew metric of a particular image frame, causes the auto-exposure management of the image frame to be performed in a manner that does not make a special provision for color bias of the content of the image frame. On the other hand, if the color-skew metric exceeds the threshold, the auto-exposure management may make special provision for the color bias represented by the color-skew metric.

At operation 206, apparatus 100 may determine a frame auto-exposure target based on the output of the adaptive target control function determined at operation 204. In certain examples, apparatus 100 may also determine one or more other auto-exposure data points (e.g., a frame auto-exposure value, etc.) at operation 206 or as part of an additional operation not explicitly shown in FIG. 2. Since the output of the adaptive target control function is determined with the color-skew metric of the image frame as an input to the function, it may also be the case that, at operation 206, apparatus 100 can be said to determine the frame auto-exposure target based on the color-skew metric determined at operation 202.

An auto-exposure value will be understood to represent certain auto-exposure-related characteristics (e.g., luminance, signal intensity, etc.) of a particular image frame or portion thereof (e.g., region, pixel, group of pixels, etc.). For example, apparatus 100 may detect such characteristics by analyzing the image frame captured by the image capture system. A pixel auto-exposure value may refer to a luminance determined for an individual pixel or an average luminance determined for a group of pixels in an implementation in which pixels are grouped together into pixel cells in a grid, or the like. As another example, a frame auto-exposure value may refer to an average luminance of some or all of the pixels or pixel groups included within an image frame such that the frame auto-exposure value corresponds to the image frame in an analogous way as a pixel auto-exposure value corresponds to a particular pixel or group of pixels.

In these examples, it will be understood that the average luminance (and/or one or more other average exposure-related characteristics in certain examples) referred to by an auto-exposure value may be determined as any type of average as may serve a particular implementation. For instance, an average auto-exposure value for an image frame may refer to a mean luminance of pixels in the image frame, determined by summing respective luminance values for each pixel or pixel group of the image frame and then dividing the sum by the total number of values. As another example, an average auto-exposure value for an image frame may refer to a median luminance of pixels in the image frame, determined as the central luminance value when all the respective luminance values for each pixel or pixel group are ordered by value. As yet another example, an average auto-exposure value for an image frame may refer to a mode luminance of pixels in the image frame, determined as whichever luminance value, of all the respective luminance values for each pixel or pixel group, is most prevalent or repeated most often. In other examples, other types of averages (besides mean, median, or mode) and/or other types of exposure-related characteristics (besides luminance) may also be used to determine an auto-exposure value in any manner as may serve a particular implementation.

An auto-exposure target will be understood to refer to a target (e.g., a goal, a desirable value, an ideal, an optimal value, etc.) for the auto-exposure value of a particular image frame or portion thereof (e.g., region, pixel, pixel group, etc.). Apparatus 100 may determine auto-exposure targets based on the particular circumstances and any suitable criteria, and the auto-exposure targets may relate to the same auto-exposure-related characteristics (e.g., luminance, signal intensity, etc.) as are represented by the auto-exposure values. For example, auto-exposure targets may be determined at desirable levels of luminance (or other exposure-related characteristics) such as a luminance level associated with middle gray or the like. As such, a pixel auto-exposure target may refer to a desired target luminance determined for an individual pixel or an average desired target luminance determined for a group of pixels in an implementation in which pixels are grouped together into pixel cells in a grid, or the like. As another example, a frame auto-exposure target may refer to an average desired target luminance for some or all of the pixels or pixel groups included within the image frame, and, as such, may represent an auto-exposure target that corresponds to the image frame in an analogous way as a pixel auto-exposure target corresponds to a particular pixel or group of pixels. Similarly as described above in relation to how frame auto-exposure values may be determined, frame auto-exposure targets in such examples may be determined by averaging individual pixel auto-exposure targets using a mean, median, mode, or other suitable type of averaging technique.

As described above, various issues (e.g., overexposure issues, channel saturation issues, etc.) may arise when image frames are significantly biased or skewed to one particular color (e.g., a low luminance color such as red) and auto-exposure targets are determined without regard for this color skew. Accordingly, a raw frame auto-exposure target determined at operation 206 based on the criteria described above (e.g., targeting middle gray, etc.) may be adjusted (e.g., scaled) to account for color bias of the image frame as quantified by the color-skew metric determined at operation 202 and in a manner defined by the adaptive target control function whose output is determined at operation 204. Specific examples of how the frame auto-exposure target may be determined based on the color-skew metric and the adaptive target control function will be provided in more detail below.

At operation 208, apparatus 100 may update (e.g., adjust or maintain) one or more auto-exposure parameters for use by the image capture system to capture one or more additional image frames. In some examples, apparatus 100 may update the one or more auto-exposure parameters based on auto-exposure values, auto-exposure targets, and/or other auto-exposure data points of the pixels of the image frame as those data points have been determined (e.g., at operation 206). For instance, assuming that apparatus 100 has determined an auto-exposure value for the image frame (a frame auto-exposure value) and an auto-exposure target for the image frame (a frame auto-exposure target), apparatus 100 may update the one or more auto-exposure parameters at operation 208 based on the frame auto-exposure value and/or frame auto-exposure target. For example, apparatus 100 may determine an auto-exposure gain for the image frame (a frame auto-exposure gain) based on the frame auto-exposure value and frame auto-exposure target, and may perform the updating of the one or more auto-exposure parameters based on the frame auto-exposure gain.

Apparatus 100 may update the auto-exposure parameters by either adjusting the parameters or maintaining the parameters as appropriate based on the auto-exposure gain. In this way, the image capture system may capture one or more additional image frames (e.g., subsequent image frames in an image frame sequence being captured) using auto-exposure parameters (e.g., exposure time parameters, shutter aperture parameters, illumination intensity parameters, image signal analog and/or digital gains, etc.) that may reduce any difference between auto-exposure values detected for those additional image frames and auto-exposure targets desirable for those additional image frames. Accordingly, the additional image frames may be captured with more desirable exposure characteristics than might be captured without such adjustments, and users of apparatus 100 may experience a superior image (e.g., an image that shows details at a desired brightness level, etc.).

Apparatus 100 may be implemented by one or more computing devices or by computing resources of a general purpose or special purpose computing system such as will be described in more detail below. In certain embodiments, the one or more computing devices or computing resources implementing apparatus 100 may be communicatively coupled with other components such as an image capture system used to capture the image frames that apparatus 100 is configured to process. In other embodiments, apparatus 100 may be included within (e.g., implemented as a part of) an auto-exposure management system. Such an auto-exposure management system may be configured to perform all the same functions described herein to be performed by apparatus 100 (e.g., including the operations of method 200, described above), but may further incorporate additional components such as the image capture system so as to also be able to perform the functionality associated with these additional components.

Figure 3:
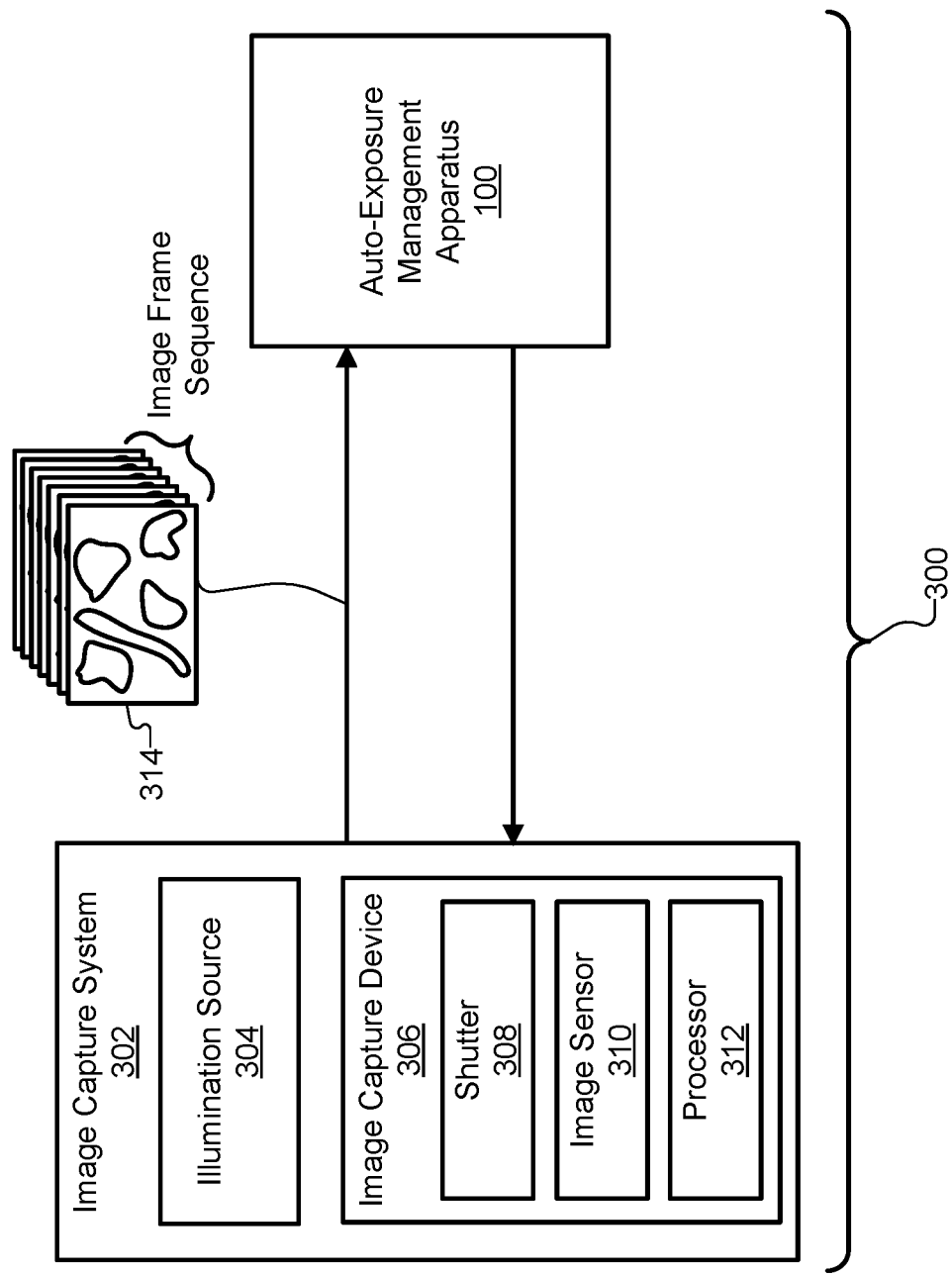
FIG. 3 shows an illustrative auto-exposure management system for managing auto-exposure of image frames according to principles described herein.

FIG. 3 shows an illustrative auto-exposure management system 300 (system 300) for managing auto-exposure of image frames. As shown, system 300 may include an implementation of apparatus 100 together with an image capture system 302 that includes an illumination source 304 and an image capture device 306 that incorporates a shutter 308, an image sensor 310, and a processor 312 (e.g., one or more image signal processors implementing an image signal processing pipeline). Within system 300, apparatus 100 and image capture system 302 may be communicatively coupled to allow apparatus 100 to direct image capture system 302 in accordance with operations described herein, as well as to allow image capture system 302 to capture and provide to apparatus 100 an image frame sequence 314 and/or other suitable captured image data. Components of image capture system 302 will now be described.

Illumination source 304 may be implemented to source any type of illumination (e.g., visible light, infrared or near-infrared light, fluorescence excitation light, etc.) and may be configured to interoperate with image capture device 306 within image capture system 302. For example, illumination source 304 may provide a certain amount of illumination to a scene to facilitate image capture device 306 in capturing optimally illuminated images of the scene. As has been mentioned, while principles described herein may be applied to a wide variety of imaging scenarios, many examples explicitly described herein relate to medical procedures that may be performed using a computer-assisted medical system such as will be described in more detail below in relation to FIG. 10. In such examples, the scene for which images are being captured may include an internal view of a body on which the medical procedure is being performed (e.g., a body of a live animal, a human or animal cadaver, a portion of human or animal anatomy, tissue removed from human or animal anatomies, non-tissue work pieces, training models, etc.), and system 300 or certain components thereof (e.g., image capture system 302) may be integrated with (e.g., implemented by imaging and computing resources of) a computer-assisted medical system. In such examples, the particular color to which captured image frames skew may include a red color (e.g., a color associated with blood ubiquitously featured in the internal view of the body).

Image capture device 306 may be implemented by any suitable camera or other device configured to capture images of a scene. For instance, in a medical procedure example, image capture device 306 may be implemented by an endoscopic image capture device configured to capture image frame sequence 314, which may include an image frame depicting a view (e.g., an internal view) of the body undergoing the medical procedure. As shown, image capture device 306 may include components such as shutter 308, image sensor 310, and processor 312.

Image sensor 310 may be implemented by any suitable image sensor, such as a charge coupled device (CCD) image sensor, a complementary metal-oxide semiconductor (CMOS) image sensor, or the like.

Shutter 308 may interoperate with image sensor 310 to assist with the capture and detection of light from the scene. For example, shutter 308 may be configured to expose image sensor 310 to a certain amount of light for each image frame captured. Shutter 308 may comprise an electronic shutter and/or a mechanical shutter. Shutter 308 may control how much light image sensor 310 is exposed to by opening to a certain aperture size defined by a shutter aperture parameter and/or for a specified amount of time defined by an exposure time parameter. As will be described in more detail below, these shutter-related parameters may be included among the auto-exposure parameters that apparatus 100 is configured to update.

Processor 312 may be implemented by one or more image signal processors configured to implement at least part of an image signal processing pipeline. Processor 312 may process auto-exposure statistics input (e.g., by tapping the signal in the middle of the pipeline to detect and process various auto-exposure data points and/or other statistics), perform optics artifact correction for data captured by image sensor 310 (e.g., by reducing fixed pattern noise, correcting defective pixels, correcting lens shading issues, etc.), perform signal reconstruction operations (e.g., white balance operations, demosaic and color correction operations, etc.), apply image signal analog and/or digital gains, and/or perform any other functions as may serve a particular implementation. Various auto-exposure parameters may dictate how the functionality of processor 312 is to be performed. For example, auto-exposure parameters may be set to define the analog and/or digital gains processor 312 applies, as will be described in more detail below.

In some examples, an endoscopic implementation of image capture device 306 may include a stereoscopic endoscope that includes two full sets of image capture components (e.g., two shutters 308, two image sensors 310, etc.) to accommodate stereoscopic differences presented to the two eyes (e.g., left eye and right eye) of a viewer of the captured image frames. Conversely, in other examples, an endoscopic implementation of image capture device 306 may include a monoscopic endoscope with a single shutter 308, a single image sensor 310, and so forth.

Apparatus 100 may be configured to control various auto-exposure parameters of image capture system 302 and may adjust such auto-exposure parameters in real time based on incoming image data captured by image capture system 302. As mentioned above, certain auto-exposure parameters of image capture system 302 may be associated with shutter 308 and/or image sensor 310. For example, apparatus 100 may direct shutter 308 in accordance with an exposure time parameter corresponding to how long the shutter is to allow image sensor 310 to be exposed to the scene, a shutter aperture parameter corresponding to an aperture size of shutter 308, or any other suitable auto-exposure parameters associated with shutter 308. Other auto-exposure parameters may be associated with aspects of image capture system 302 or the image capture process unrelated to shutter 308 and/or sensor 310. For example, apparatus 100 may adjust an illumination intensity parameter of illumination source 304 that corresponds to an intensity of illumination provided by illumination source 304, an illumination duration parameter corresponding to a time period during which illumination is provided by illumination source 304, or the like. As yet another example, apparatus 100 may adjust gain parameters corresponding to one or more analog and/or digital gains (e.g., analog gains, bayer gains, RGB gains, etc.) applied by processor 312 to luminance data generated by image sensor 310.

Any of these or other suitable parameters, or any combination thereof, may be updated and/or otherwise adjusted by apparatus 100 for subsequent image frames based on an analysis of the current image frame. For instance, in one example where the frame auto-exposure gain (e.g., the frame auto-exposure target divided by the frame auto-exposure value) is determined to be 6.0, various auto-exposure parameters could be set as follows: 1) a current illumination intensity parameter may be set to 100% (e.g., maximum output); 2) an exposure time parameter may be set to $\frac{1}{60}^{th}$ of a second (e.g., 60 fps); 3) an analog gain may be set to 5.0 (with a cap of 10.0); 4) a bayer gain may be set to 1.0 (with a cap of 3.0); and 5) an RGB gain may be set to 2.0 (with a cap of 2.0). With these settings, the gain is distributed across the analog gain (10.0/5.0=2.0), bayer gain (3.0/1.0=3.0), and RGB gain (2.0/2.0=1.0) to establish the desired 6.0 total auto-exposure gain (3.0*2.0*1.0=6.0) for the frame.

Figure 4:
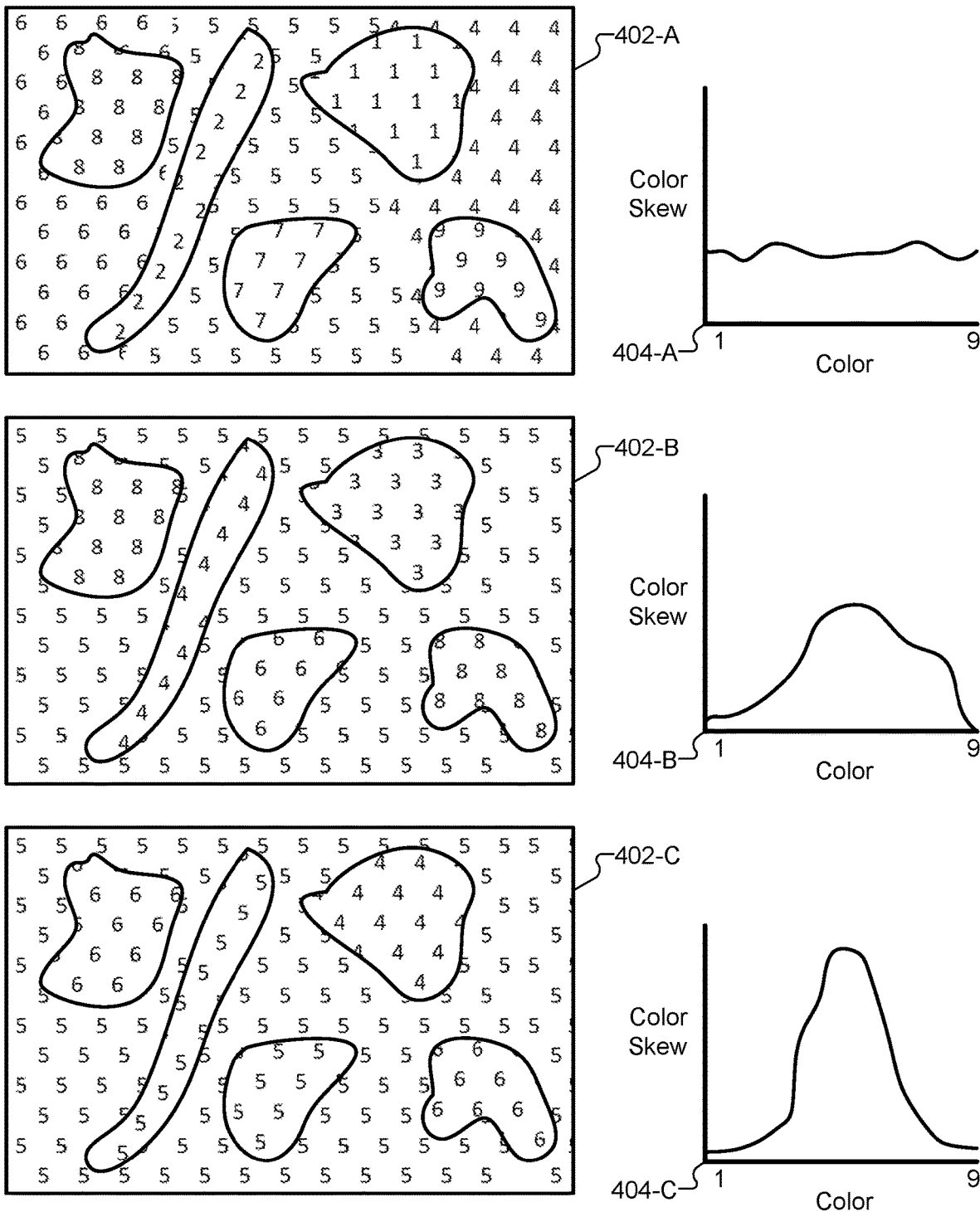
FIG. 4 shows illustrative image frames and color skew characteristics of the image frames according to principles described herein.

FIG. 4 shows illustrative image frames 402 (e.g., image frame 402-A through 402-C) and respective color skew characteristics 404 (e.g., color skew characteristics 404-A through 404-C) of the respective image frames. More specifically, as shown, a first image frame 402-A represents an illustrative image frame depicting content that is relatively neutral in terms of color skew (e.g., the content is not significantly skewed toward any particular color more than any other color). A second image frame 402-B represents an illustrative image frame depicting content that skews to a particular color over other colors to a limited extent. A third image frame 402-C represents an illustrative image frame depicting content that skews to the particular color to a greater extent. For example, image frame 402-B and/or 402-C could represent image frames depicting an internal view of a body and the particular color to which their content skews (albeit to different extents) could be a red color associated with blood depicted in the internal view of the body.

While FIG. 4 is depicted as a black and white drawing, various digits 1-9 used to fill the various shapes and background areas depicted in image frames 402 will be understood to represent different colors. In this digit-based color notation, digits closer to one another (e.g., 1 and 2, 8 and 9, etc.) will be understood to represent similar colors (e.g., red and red-orange, green and green-yellow, etc.), while digits farther away from one another (e.g., 1 and 8, 2 and 9, etc.) will be understood to represent more distinct colors (e.g., red and green, blue and orange, etc.). In some examples, this digit-based color notation may be interpreted to wrap around such that digit 1 is considered to adjacent to digit 9 and color represented by digit 1 is similar to color represented by digit 9.

Next to each image frame 402, a graph showing color skew characteristics 404 is drawn. In these graphs, the x-axis represents the different colors represented by digits 1-9 while the y-axis represents an extent to which the image frame is skewed to those colors. Accordingly, as illustrated by color skew characteristics 404-A corresponding to image frame 402-A, image frame 402-A does not skew particularly to any color (e.g., as evidenced by the absence of any major peaks or valleys in the graph plot) but is instead fairly neutral (e.g., made up of colors all along the spectrum as evidenced by the relatively flat graph plot).

In contrast, as illustrated by color skew characteristics 404-B corresponding to image frame 402-B, image frame 402-B does skew somewhat to colors in the middle-to-upper part of the color spectrum (e.g., color represented by digits 5-8 or so) as evidenced by the valleys on the left and far-right sides of the graph plot and the peak in the middle-to-upper part of the graph plot. If digit 5 represents a red color, for example, the color skew characteristics 404-B may indicate that image frame 402-B includes a lot of reds and oranges and possibly yellows without necessarily a lot of greens and blues or the like.

Even more evidently, as illustrated by color skew characteristics 404-C corresponding to image frame 402-C, image frame 402-C may skew to a great extent to colors in the middle part of the color spectrum (e.g., color represented by digits 4-6 and especially digit 5) as evidenced by the conspicuous peak in the middle of the graph plot and the valleys elsewhere along the graph plot. In this example, if digit 5 again represents the red color, color skew characteristic 404-C indicates that image frame 402-C is highly skewed or biased toward various shades of red (e.g., red, pink, reddish-orange, reddish-violet, etc.) as might be the case for an internal view of a body that depicts blood and bloody tissue pervasive at a scene of a medical procedure.

Auto-exposure management described herein may be configured to apply no special color-skew functionality to a relatively neutral image frame such as image frame 402-A. However, as will be described in more detail below, auto-exposure management described herein may account for the relatively mild color skew of image frame 402-B and the more significant color skew of image frame 402-C in ways that progressively account for the color skew in the determination of frame auto-exposure targets for these image frame. Ultimately, accounting for the frame auto-exposure targets in these ways may lead to more beneficial updating of auto-exposure parameters for image capture systems capturing image frame sequences at these color-skewed scenes.

Figure 5:
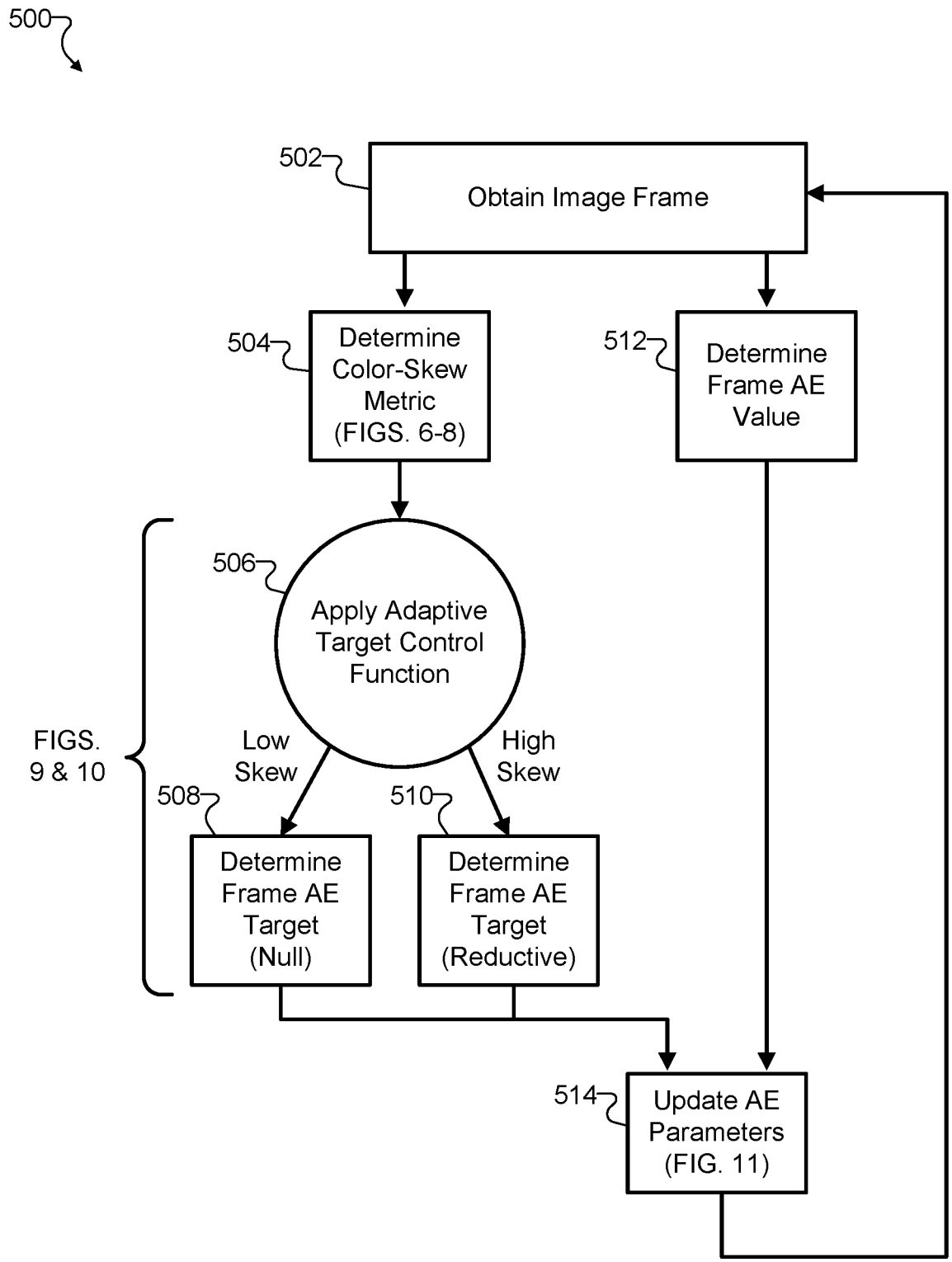
FIG. 5 shows an illustrative flow diagram for managing auto-exposure of image frames according to principles described herein.

FIG. 5 shows an illustrative flow diagram 500 for managing auto-exposure of image frames using, for example, an implementation of apparatus 100, method 200, and/or system 300. As shown, flow diagram 500 illustrates various operations 502-514, which will each be described in more detail below. It will be understood that operations 502-514 represent one embodiment, and that other embodiments may omit, add to, reorder, and/or modify any of these operations. As will be described, various operations 502-514 of flow diagram 500 may be performed for one image frame or multiple image frames (e.g., each image frame) in an image frame sequence. It will be understood that, depending on various conditions, not every operation might be performed for every frame, and the combination and/or order of operations performed from frame to frame in the image frame sequence may vary.

At operation 502, an image frame captured by an image capture system may be obtained (e.g., accessed, loaded, captured, generated, etc.). As previously explained, in certain examples, the image frame may be an image frame depicting image content that is color-biased to at least some extent (e.g., to a very small extent n the case of neutral content and to a relatively large extent in the case of content that skews heavily to a particular color). For example, the obtained image frame may be similar to any of image frames 402 described above. Operation 502 may be performed in any suitable way, such as by accessing the image frame from an image capture system (e.g., in the case that operation 502 is being performed by an implementation of apparatus 100 that is communicatively coupled to an image capture system) or by using an integrated image capture system to capture the image frame (e.g., in the case that operation 502 is being performed by an implementation of system 300 that includes integrated image capture system 302).

At operation 504, apparatus 100 may determine a color-skew metric for the image frame obtained at operation 502. For example, as mentioned above, the color-skew metric may be a quantified representation indicative of the extent to which the image frame skews to a particular color. In certain implementations, the auto-exposure management being performed may be configured to identify skew to a single particular color (e.g., red in the case of an implementation used for endoscopic imagery commonly depicting bloody medical scenes within bodies). Accordingly, the color-skew metric in these examples may indicate how skewed the image frame may be to that particular color. In other implementations, the auto-exposure management being performed may be configured to identify skew to any color (instead of to a certain color). Accordingly, the color-skew metric in these examples may indicate how skewed the image frame is to any one color (e.g., as opposed to how neutral the image frame may be relative to many colors). As indicated in FIG. 5, FIGS. 6-8 further illustrate how color skew may be analyzed and quantified as the color-skew metric is determined at operation 504.

Figure 6:
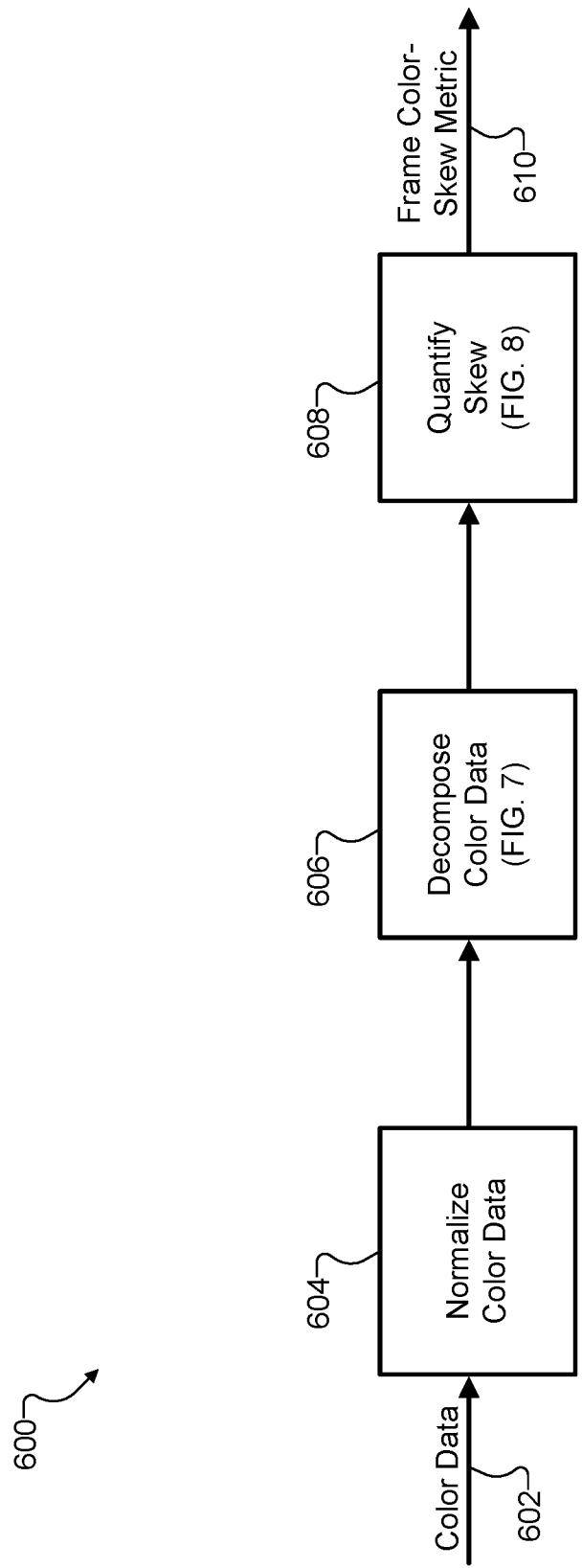
FIG. 6 shows an illustrative technique for determining a color-skew metric for an image frame according to principles described herein.

FIG. 6 shows an illustrative technique 600 for determining a color-skew metric for an image frame and further references concepts illustrated by FIGS. 7 and 8, as described below. As shown, color data 602 may be used as an input for technique 600. Color data 602 may be associated with the image frame obtained at operation 502 described above and may be represented in any suitable color space (e.g., color data format), such as a Red-Green-Blue (RGB) color space, used by the image capture system when the image frame is captured and provided to apparatus 100. Color data 602 may then be processed in multiple stages (e.g., a normalize color data stage 604, a decompose color data stage 606, and/or a quantify skew stage 608) so that, ultimately, color data 602 may form the basis of a frame color-skew metric 610 that is an output of technique 600.

At stage 604, apparatus 100 may normalize color data 602 so that bias caused by luminance scaling may be avoided. Regardless of how color data 602 is represented, color data 602 may in some manner represent both luminance data (associated with how bright each pixel is regardless of color) and chrominance data (associated with what color each pixel is regardless of brightness). In certain color spaces and color data formats, luminance and chrominance data are represented separately, while, in other color spaces and color data formats, the concepts are represented in a manner that merges these concepts in ways that may provide convenience in image capture, image rendering, or the like. One example of a color space that merges chrominance and luminance concepts in its data representation is the RGB color space, which jointly represents chrominance and luminance characteristics in three values—an 'R' value associated with a red channel, a 'G' value associated with a green channel, and a 'B' value associated with a blue channel. In the RGB color space, two pixels that are equally red in terms of their chrominance characteristics may thus have different 'R' values if the pixels are not of equal brightness.

By normalizing the color data at stage 604, color data represented in a color space such as RGB may effectively be put on an even playing field in terms of luminance characteristics of each pixel so that chrominance characteristics of each pixel may be analyzed irrespective of the luminance characteristics. It may be desirable for the color-skew metric determined by technique 600 to determine the extent to which pixels and frames skew to a particular chrominance irrespective of luminance characteristics. For example, it may be desirable for a bright white pixel to be treated as a neutral pixel and for a dark red pixel to be treated as a red-skewed pixel despite the fact that, in color spaces such as RGB, the bright white pixel may be associated with a greater 'R' value than the dark red pixel (due only to their different luminance characteristics). One way to normalize color data in the RGB color space may be to determine the maximum of the 'R', 'G', and 'B' values and generate the normalized value on that basis. In the example of the bright white pixel and the dark red pixel described above, for instance, the maximum value for the dark red pixel may be red (the 'R' value) by a significant margin, while the bright white pixel may not have a maximum value (or at least not a significant margin) since the 'R', 'G', and 'B' values in this case may all be very similar.

At stage 606, apparatus 100 may decompose the normalized color data to distinguish a chrominance property of the color data from a luminance property of the color data. For example, the normalized color data for each pixel may be decomposed from the RGB color space described above into a different color space that accounts for primary, secondary, and/or tertiary colors and that separately accounts for luminance characteristics. As one example, the decomposing of the color data at stage 606 may include converting the color data from an RGB color space to a Cyan-Magenta-Yellow-blacK-Red-Green-Blue (CMYKRGB) color space. As another example, the decomposing of the color data at stage 606 may include converting the color data to a YUV color space, a CIELAB color space, or another suitable color space that allows for the color data to be conveniently analyzed in a manner that is exposure independent (e.g., in a manner that represents luminance and chrominance characteristics separately).

Figure 7:
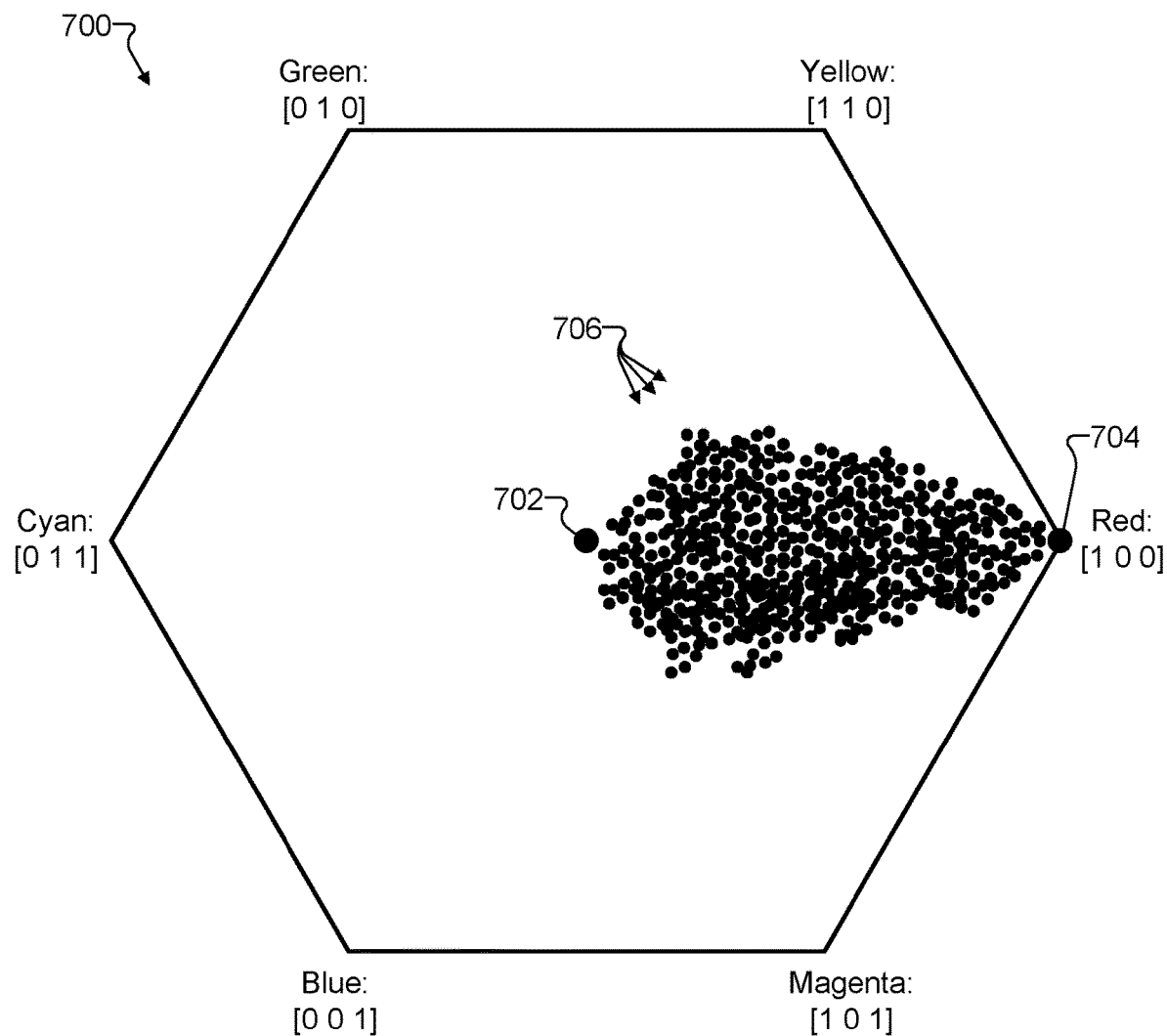
FIG. 7 shows an illustrative diagram depicting chrominance characteristics of decomposed color data according to principles described herein.

To further illustrate these concepts, FIG. 7 shows an illustrative diagram 700 depicting exposure-independent chrominance characteristics of decomposed color data. As shown, diagram 700 includes a barycentric plot of color data that has been converted into a color space such as CMYKRGB. It will be understood that similar plots for other suitable color spaces (e.g., a YUV color space, a CIELAB color space, etc.) may illustrate similar principles as shown here by the CMYKRGB plot since each of these color spaces likewise enables chrominance properties to be conveniently analyzed independently of luminance properties.

In the example of FIG. 7, simulated human tissue color is represented so as to illustrate a plot that may be expected for an endoscopic image frame depicting an internal view of a body. In diagram 700, a neutral point 702 is shown in the center of the plot to represent pixels that are neutral (e.g., black, white, or any shade of gray) and hence do not skew any more to one primary or secondary color (e.g., red, magenta, blue, cyan, green, or yellow) than to any other. Diagram 700 also shows a point 704 at a vertex labeled Red to represent pixels that are purely red and do not include any aspect of any other primary or secondary color. As shown, a large number of respective points 706 illustrate where each pixel of a particular image frame depicting an internal view of a body may be plotted within diagram 700. Virtually every point in this example is shown to skew toward the Red vertex (e.g., to congregate along a neutral-red hue line connecting points 702 and 704) to one extent or another, as opposed to exhibiting strong characteristics associated with other primary or secondary colors. Accordingly, the image frame represented by diagram 700 may appear as a very red-biased image frame such as may be expected for imagery captured within a body by an endoscope.

Returning to FIG. 6, at stage 608, apparatus 100 may quantify the color skew to determine frame color-skew metric 610. For example, apparatus 100 may determine an extent to which the chrominance property of the color data skews to the particular color and, based on this determination of the extent to which the chrominance property of the color data skews to the particular color, may determine frame color-skew metric 610. As one example, based on the image frame represented by diagram 700 in FIG. 7, stage 608 may analyze chrominance characteristics of each pixel of the image frame associated with each point 706 to thereby quantify how red the image frame is in an objective manner (e.g., to determine a skew quantity that indicates an objective measure of the extent to which the image frame skews toward the red color in this example).

Figure 8:
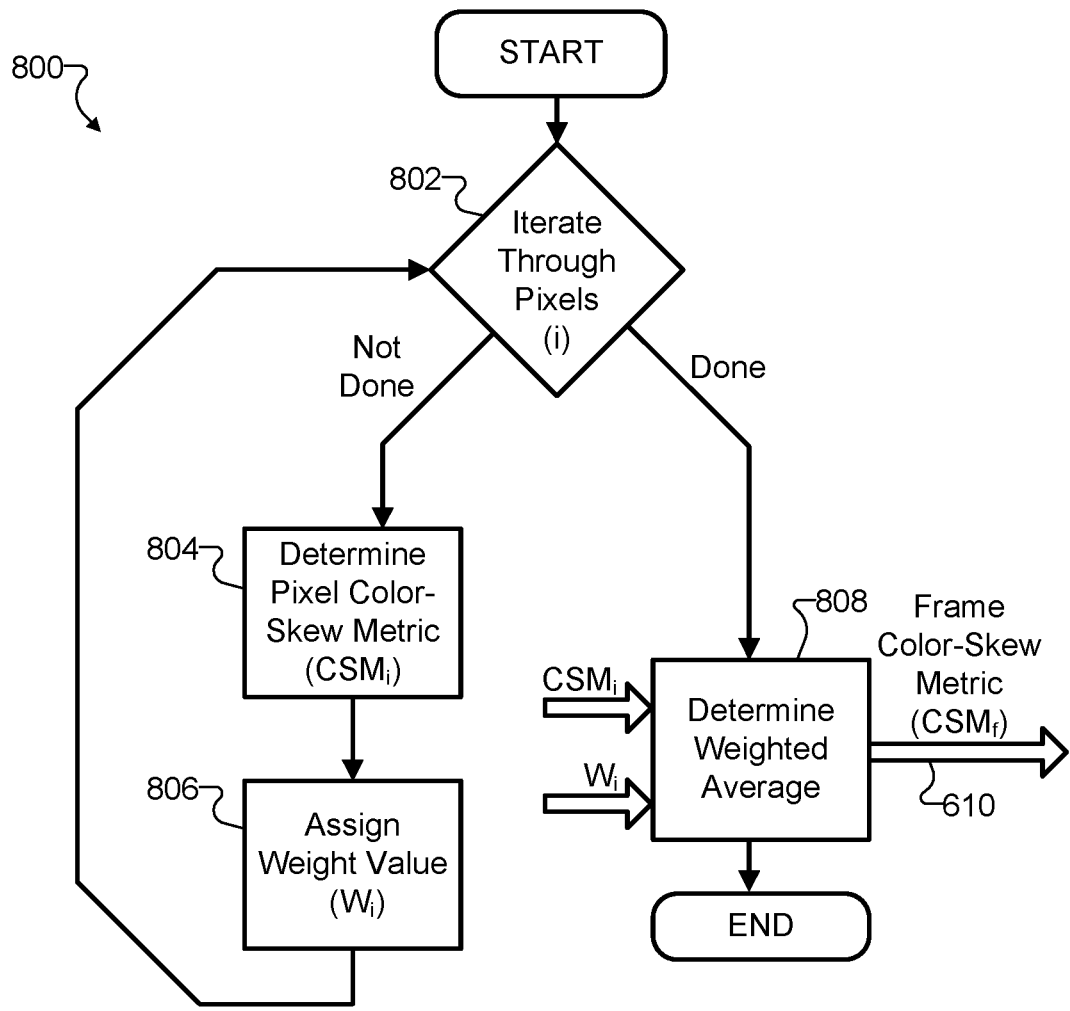
FIG. 8 shows an illustrative flow diagram for quantifying color skew as part of a determination of a color-skew metric according to principles described herein.

To illustrate how this quantifying determination may be performed at stage 608, FIG. 8 shows an illustrative flow diagram 800 for quantifying color skew as part of a determination of a color-skew metric. As shown, flow diagram 800 includes a plurality of operations 802-808 that may be performed between when apparatus 100 arrives at stage 608 (labeled START) and when flow diagram 800 is complete and the frame color-skew metric 610 is determined (labeled END).

At operation 802, apparatus 100 may iterate through each pixel of an image frame or portion of an image frame. For each pixel i, a pixel color-skew metric ($CSM_i$) may be determined at operation 804 and a weight value ($W_i$) may be assigned at operation 806. As shown, this may continue for as long as there are still pixels of the image frame that have not yet been analyzed (Not Done), and may end when all of the pixels of the image frame have been iterated through (Done). In certain examples, as has been mentioned, pixels may be processed in groups (e.g., cells of a grid into which the pixels are divided, etc.) rather than individually. Accordingly, rather than determining a pixel color-skew metric and weight value for each individual pixel, it will be understood that these implementations may determine a pixel color-skew metric and weight value for each pixel group. Additionally, in some implementations, rather than iterating through all of the pixels (or pixel groups) of the image frame, a certain region of the image frame (e.g., a central region of the image frame such as a central 50% of the image frame, a central 80% of the image frame, etc.) may be accounted for while another region of the image frame (e.g., a peripheral region of the image frame such as an outer 50% of the image frame, an outer 20% of the image frame, etc.) may be ignored for purposes of auto-exposure management. In such examples, operation 802 may finish iterating (Done) when all the pixels of the region that is to be accounted for (e.g., the central region) have been iterated through.

At operation 804, apparatus 100 may determine pixel color-skew metrics for the pixels included in the image frame (e.g., one pixel color-skew metric per pixel) in any suitable manner. The pixel color-skew metrics determined at operation 804 may be objective, quantitative measures of an extent to which the pixels skew to a particular color (e.g., red, etc.). For example, each pixel (or pixel group) may be associated with a particular point 706 shown on diagram 700 and the pixel color-skew metric may be determined based on a linear distance of the particular point 706 to the neutral point 702 (e.g., the larger the distance, the greater the pixel color-skew metric), to the red point 704 (e.g., the smaller the distance, the greater the pixel color-skew metric), a combination thereof, or the like. As has been mentioned, the red color is only an example, so in other implementations, the pixel color-skew metric may be determined based on the proximity of a point 706 to another color point rather than the red color point 704. Additionally, as has been mentioned, the CMYKRGB color space illustrated in FIG. 7 is to be understood to be only one example of a color space into which the pixels of the image frame may be decomposed and points 706 plotted. Other suitable color spaces (e.g., YUV, CIELAB, etc.) that similarly represent chrominance characteristics in a manner separate from luminance therefore may also be used to geometrically determine how close a pixel point is to a particular color within the color space.

At operation 806, each of the plurality of pixels of the image frame or region thereof (e.g., each pixel i) may be assigned a weight value based on spatial positions of the plurality of pixels within the image frame. The weight values assigned at operation 806 may reflect how likely each pixel is to be within an area of focus of a viewer of the image frame, and, thus, how relatively important each pixel is considered to be with respect to other pixels in the image frame. For example, in certain implementations, it may be assumed that the viewer is likely to focus attention near a center of the image frame, so each pixel may be assigned a weight indicative of proximity to the center of the image frame (e.g., with higher weight values indicating closer proximity to the center and lower weight values indicating a farther distance from the center). As another example, an implementation could include an eye tracking feature to determine in real time what part of the image frames the viewer is focusing on, and each pixel could be assigned a weight indicative of a proximity to the detected real-time area of focus (e.g., rather than or in addition to the center of the image frame). In still other examples, pixels may be weighted in accordance with other spatial-position-based criteria (e.g., proximity to an object of interest that moves around within the image frame, proximity to another assumed area of focus within the image frame other than the center, etc.) or non-spatial-position-based criteria. Alternatively, each pixel may be treated as equally important regardless of its spatial position and no weight value may be assigned (e.g., operation 806 may be omitted entirely).

Because operations 804 and 806 might not be dependent on one another, these operations may be performed for each pixel (or pixel group) i independently and in any order or in parallel with one another. In some examples, the assigning of the weight value to each pixel at operation 806 may be only performed once (e.g., assigning a static value to be used for each image frame or an image frame sequence) even as the pixel color-skew metric may be reevaluated and determined at operation 804 dynamically for each image frame. In other examples, both operations 804 and 806 may be performed dynamically for each image frame.

Once all of the pixels i of the image frame (or a portion thereof) have been iterated through at operation 802, flow may proceed (Done) to operation 808. At operation 808, apparatus 100 may determine frame color-skew metric 610 as a weighted average of the pixel color-skew metrics. For example, as shown by inputs to operation 808, color-skew metric 610 may be determined based on both the pixel color-skew metrics ($CSM_i$) and the assigned weight values ($W_i$). Just as each pixel color-skew metric may correspond to the extent to which a pixel (or pixel group) skews toward the particular color, frame color-skew metric 610 may correspond to the extent to which the image frame is determined to skew toward the particular color. Because the weighted average is used, the frame color-skew metric may indicate a higher extent of color skew when higher weighted pixels (e.g., central pixels, etc.) are skewed toward the particular color than when lower weighted pixels (e.g., peripheral pixels, etc.) are skewed toward the particular color. The weighted average may be calculated using any type of suitable averaging methodology (e.g., a mean average, a median average, a mode average, a combination thereof, etc.) and may incorporate the weight values to give more emphasis to higher-weighted pixels than to lower-weighted pixels in any manner as may serve a particular implementation. As previously explained, weight values might not be used or the pixels in the image frame (or portion of the image frame) may use the same weight value (e.g., 1). In these scenarios, frame color-skew metric 610 may depend on the pixel color-skew metrics ($CSM_i$) but might not depend on the weight values ($W_i$).

Returning to FIG. 6, frame color-skew metric 610 is shown to be the output of technique 600 for determining the color-skew metric based on the quantifying of the color skew performed at stage 608. Accordingly, returning to FIG. 5, apparatus 100 may progress from operation 504 to operation 506 once frame color-skew metric 610 has been determined.

At operation 506, apparatus 100 may apply an adaptive target control function to a frame auto-exposure target based on frame color-skew metric 610 determined at operation 504. For example, if frame color-skew metric 610 indicates that the extent to which the image frame skews to the particular color is relatively low (Low Skew), the application of the adaptive target control function at operation 506 may cause apparatus 100 to determine the frame auto-exposure target at operation 508 without making any special allowance for the color bias of the image frame. Conversely, if frame color-skew metric 610 indicates that the extent to which the image frame skews to the particular color is relatively high (High Skew), the application of the adaptive target control function at operation 506 may cause apparatus 100 to determine the frame auto-exposure target at operation 510, where reductive measures may be taken to account for the color bias of the image frame. In some examples, a frame color-skew metric 610 below a threshold color-skew metric may indicate Low Skew and/or a frame color-skew metric 610 above the threshold color-skew metric may indicate High Skew.

Figure 9:
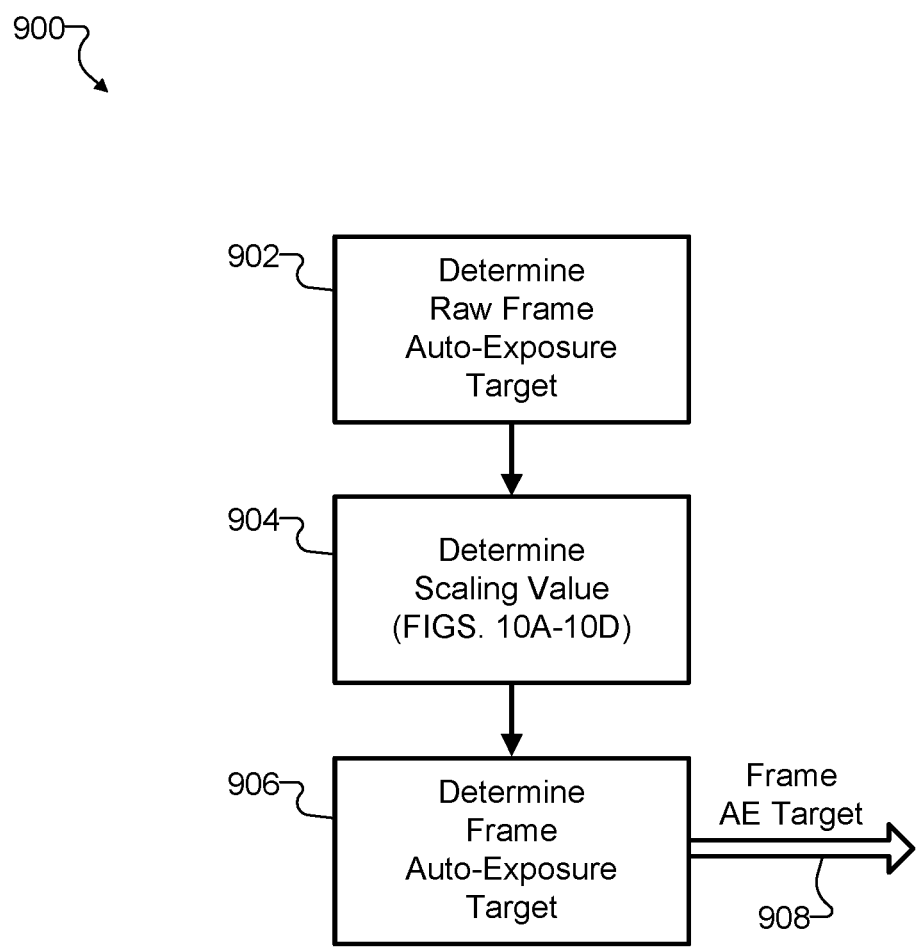
FIG. 9 shows an illustrative technique for determining a frame auto-exposure target based on a color-skew metric according to principles described herein.

To illustrate the functionality of operations 506-510 in more detail, FIG. 9 shows an illustrative technique 900 for determining a frame auto-exposure target based on a frame color-skew metric. Specifically, as shown, operations 902-906 may be performed to generate a frame auto-exposure target 908 that, based on frame color-skew metric 610, helps account for the extent of the color bias of the frame to provide the auto-exposure benefits and avoid the auto-exposure issues that have been described.

At operation 902, apparatus 100 may determine a first (e.g., raw) frame auto-exposure target based on the image frame as captured by the image capture system. For example, the raw frame auto-exposure target may be determined based on an average or weighted average of pixel auto-exposure targets determined to target an auto-exposure value associated with middle gray or the like.

At operation 904, apparatus 100 may determine a scaling value as an output of an adaptive target control function (e.g., a predetermined adaptive target control function) given an input of the color-skew metric (e.g., frame color-skew metric 610). An adaptive target control function may refer to a function designed to map various potential color-skew metrics to various desirable auto-exposure targets. For example, in certain implementations, an adaptive target control function may take a frame color-skew metric as an input and may output a scaling value that can be used to scale a raw frame auto-exposure target to result in a second (e.g., desired) frame auto-exposure target. The second frame auto-exposure target may account for the color bias to thereby avoid the exposure issues described above.

FIGS. 10A-10D show illustrative implementations of various adaptive target control functions that could be employed to account for color-biased content in various ways. In each illustrated adaptive target control function 1002 (e.g., adaptive target control function 1002-A in FIG. 10A through adaptive target control function 1002-D in FIG. 10D), the input color-skew metric (Color-Skew Metric) is represented along the x-axis with lower color-skew metric values being represented toward the left side of the axis (Low) and higher color-skew metric values being represented toward the right side of each axis (High). The output scaling value of the adaptive target control function is then represented along the y-axis. As such, a frame color-skew metric 610 determined in the ways described above may be plotted along the x-axis so that the output of the adaptive target control function 1002 can be determined based on the y-value returned by the function for the plotted x-value.

As shown in each adaptive target control function 1002, if the input color-skew metric is low enough (e.g., below a threshold color-skew metric), the scaling value returned may be a large scaling value referred to herein as a null scaling value (Null). A null scaling value may have no effect (e.g., a null effect) when used to scale a raw frame auto-exposure target. For example, if the scaling of the raw frame auto-exposure target is performed by multiplying the raw frame auto-exposure target with the scaling value, a null scaling value may have a value of 1 so as to not change the raw frame auto-exposure target when multiplied with it. However, as also shown in each adaptive target control function 1002, if the input color-skew metric is high enough (e.g. above a threshold color-skew metric), the scaling value returned may be a scaling value referred to herein as a reductive scaling value (Reductive). A reductive scaling value may have a reductive effect when used to scale a raw frame auto-exposure target. For example, if the scaling of the raw frame auto-exposure target is performed by multiplying the raw frame auto-exposure target with the scaling value, a reductive scaling value may have a value less than 1 (e.g., between 0 and 1) so as to reduce the raw frame auto-exposure target when multiplied with it. It may be desirable to reduce a raw frame auto-exposure target by a maximum amount for an image frame that has a maximum color-skew metric (e.g., a purely red image frame if the particular color is red). The maximum reductive scaling value is labeled as Full (a full reduction) in FIGS. 10A-10D and is shown to be applied for the highest color-skew metrics. Depending on the implementation, the full reductive value may be defined to be any suitable level between zero and the null scaling value (e.g., between 0 and 1).

Figure 10A:
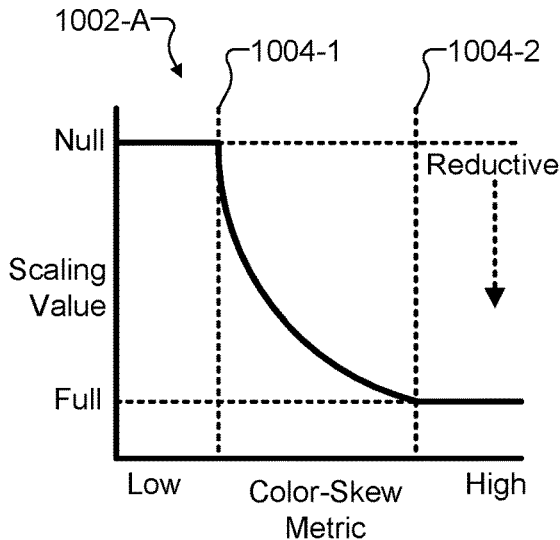
FIGS. 10A-10D show illustrative implementations of various adaptive target control functions according to principles described herein.
Figure 10B:
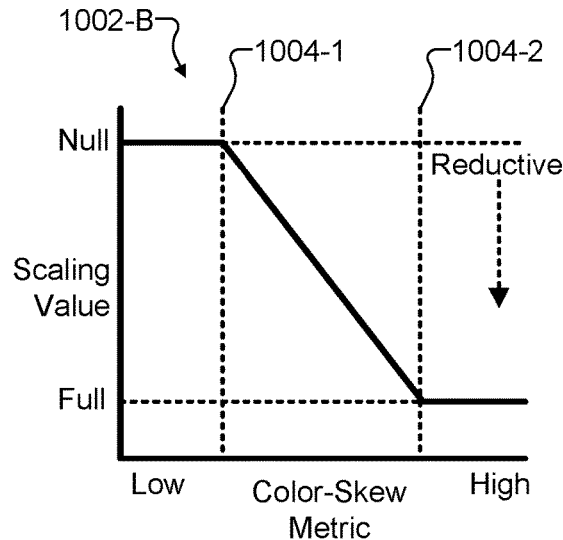

As shown in the examples of adaptive target control functions 1002-A and 1002-B in FIGS. 10A and 10B, respectively, different sections of the adaptive target control function may return the null scaling value (to produce the minimum amount of scaling of the raw frame auto-exposure target) or the full scaling value (to produce the maximum amount of scaling of the raw frame auto-exposure target). Specifically, as shown, if the color bias of the content depicted by the image frame is not skewed enough to merit special treatment, the color-skew metric given as the input might not exceed a color-skew threshold 1004-1, and the output returned by the adaptive target control function 1002 may be the null scaling value. Conversely, if the color bias of the content depicted by the image frame is heavily biased, the color-skew metric given as the input may exceed a color-skew threshold 1004-2, and the output returned by the adaptive target control function 1002 may be the full scaling value.

Between these extremes, adaptive target control functions 1002-A and 1002-B show a middle section of increasingly reductive scaling values that may be returned for color-skew metrics that exceed threshold 1004-1 but do not exceed threshold 1004-2, For example, if apparatus 100 determines that the color-skew metric given as the input exceeds color-skew threshold 1004-1 and does not exceed color skew threshold 1004-2, the output of adaptive target control function 1002-A or 1002-B may be a reductive scaling value less than the null scaling value and greater than the full reductive scaling value. For example, the output of the adaptive target control function in these scenarios may be determined based on a decreasing function, such as a monotonically decreasing function. Adaptive target control function 1002-A in FIG. 10A shows, for instance, a monotonically decreasing non-linear function (e.g., a monotonically decreasing power function), whereas adaptive target control function 1002-B in FIG. 10B shows a monotonically decreasing linear function. In other examples, other types of monotonically decreasing functions (or non-monotonically decreasing functions, in certain implementations) may be employed to provide similar results as those provided by adaptive target control functions 1002-A and 1002-B.

In certain examples, apparatus 100 may determine a color-skew metric to correspond to a value selected from a set of discrete values. For example, rather than a color-skew metric represented as a fraction or floating-point number, the color-skew metric may be implemented as a discrete value such as a binary value (e.g., 0 for insignificant color bias, 1 for significant color bias), or a value selected from a set of discrete values (e.g., values 0, 1, 2, 3, and 4 to represent a range from no color bias (0) up to very high color bias (4), etc.). In such examples, an adaptive target control function may map each discrete color-skew metric possibility to a corresponding scaling value output by the adaptive target control function for the color-skew metric.

Figure 10C:
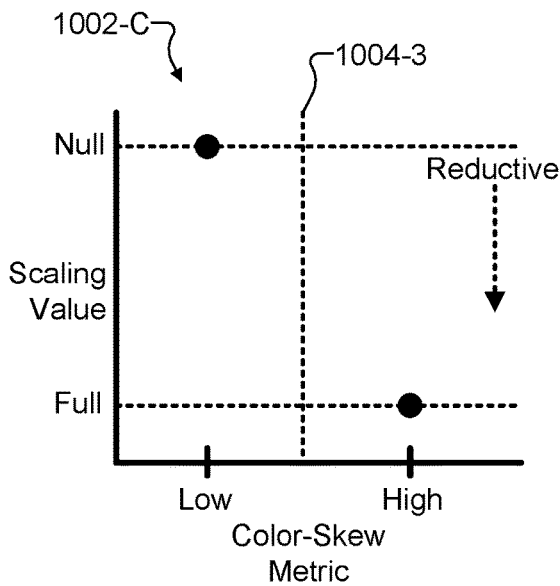
Figure 10D:
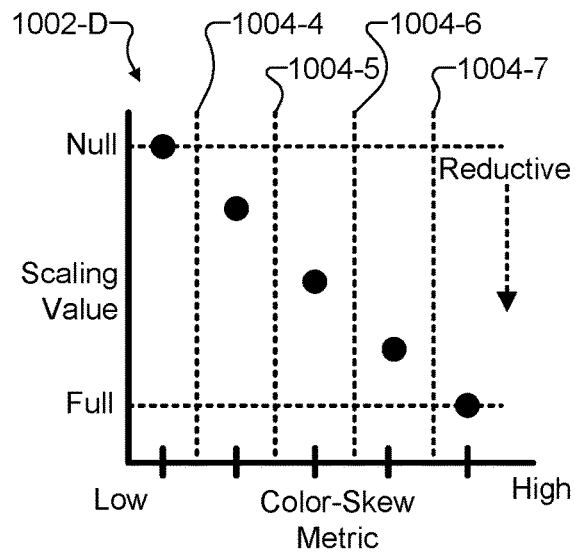

To illustrate, adaptive target control function 1002-C of FIG. 10C shows a binary example where an image frame having any amount of color skew less than a color-skew threshold 1004-3 is assigned a first binary color-skew metric (e.g., a color-skew metric of Low or zero or the like) and an image frame having any amount of color skew greater than color-skew threshold 1004-3 is assigned a second binary color-skew metric (e.g., a color-skew metric of High or one or the like). In this example, adaptive target control function 1002-C returns the null scaling value for the low color-skew metric and the full scaling value for the high color-skew metric. Similarly, adaptive target control function 1002-D of FIG. 10D shows another discrete-value implementation where a color-skew metric is assigned as one of five different values depending on where the color skew of an image frame falls with respect to several color-skew thresholds 1004-4 through 1004-7. In this example, adaptive target control function 1002-D returns the null scaling value for the lowest color-skew metric, the full scaling value for the highest color-skew metric, and varying other reductive scaling values between the null scaling value and the full scaling value for the other potential color-skew metrics.

Returning to FIG. 9, after the scaling value has been determined at operation 904 based on whatever adaptive target control function 1002 may be implemented in a particular embodiment, apparatus 100 may perform operation 906. At operation 906, apparatus 100 may determine frame auto-exposure target 908 by scaling the raw frame auto-exposure target determined at operation 902 by the scaling value determined at operation 904. For example, if the scaling value determined at operation 904 is the null scaling value, the frame auto-exposure target may be determined at operation 906 to equal the raw frame auto-exposure target determined at operation 902. Conversely, if the scaling value determined at operation 904 is a reductive scaling value (e.g., up to and including the full scaling value), the frame auto-exposure target may be determined at operation 906 to equal the raw frame auto-exposure target determined at operation 902 reduced based on the reductive scaling value. In this way, frame auto-exposure target 908 may be reduced to account for a color bias when the image frame depicts content that is skewed to a certain extent.

While the example above described a scenario in which frame auto-exposure target 908 is determined based on a non-weighted raw frame auto-exposure target and a weighted frame color-skew metric, it will be understood that the same or a similar frame auto-exposure target could be determined in alternative ways that may be employed in certain implementations. As one illustrative alternative, instead of determining the frame color-skew metric 610 ($CSM_f$) as a weighted average, and then using that weighted average to determine a scaling value to be mapped to the non-weighted raw frame auto-exposure target, apparatus 100 may determine scaling values on a pixel level and determine a weighted average of pixel auto-exposure targets that have already been scaled to account for color skew. For example, a pixel auto-exposure target may be determined for each pixel (or group of pixels) I, along with the pixel color-skew metrics $CSM_i$. A scaling value may then be determined for each pixel (or group of pixels) based on the pixel color-skew metrics and applied to the corresponding pixel auto-exposure targets. The frame auto-exposure target may then be determined based on a weighted average of these scaled pixel auto-exposure targets (which already account for color skew at each pixel). In still other implementations, frame auto-exposure targets that account for color skew and pixel weights may be determined in other alternative ways as may serve a particular implementation.

Returning to FIG. 5, operation 512 may be independent from and performed in parallel with operations 504-510. At operation 512, apparatus 100 may determine a frame auto-exposure value in any manner as may serve a particular implementation. For example, apparatus 100 may determine a pixel auto-exposure value for each pixel (or group of pixels in certain implementations) and then determine the frame auto-exposure value by averaging the pixel auto-exposure values in accordance with any suitable averaging technique (e.g., mean, median, mode, etc.). In some examples, a weighted average of the pixel auto-exposure values may be computed for the frame auto-exposure value, or an average of only pixels included within a particular region (e.g., a central region that excludes peripheral portions of the image frame) may be used.

Once a frame auto-exposure value has been determined at operation 512 and a frame auto-exposure target has been determined at operation 508 or 510, flow may move to operation 514, where apparatus 100 may update auto-exposure parameters for the image capture system based on the frame auto-exposure value and frame auto-exposure target. At operation 514, apparatus 100 may update (e.g., adjust or maintain) auto-exposure parameters of the image capture system in preparation for the image capture system capturing subsequent image frames in the image frame sequence.

Figure 11:
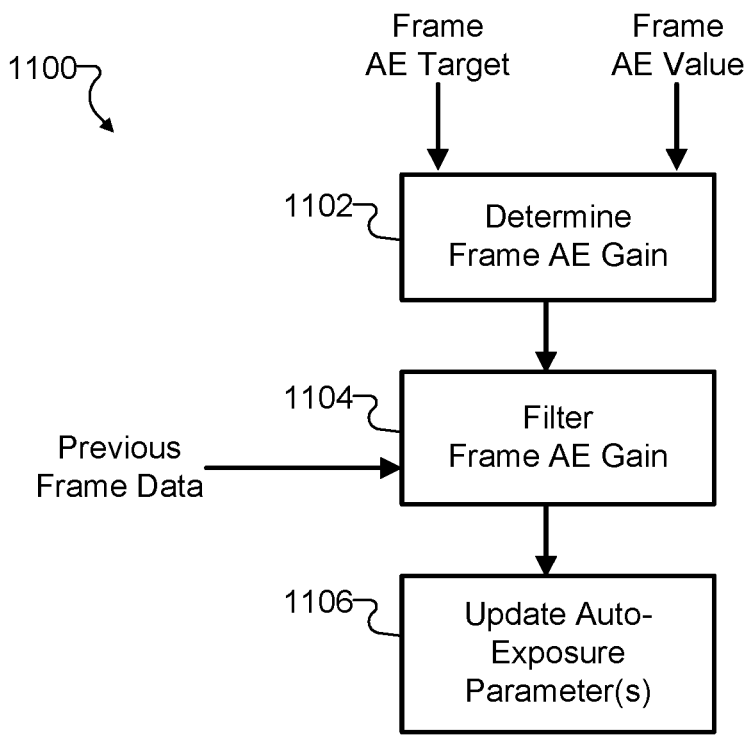
FIG. 11 shows an illustrative technique for updating an auto-exposure parameter according to principles described herein.

FIG. 11 shows an illustrative technique 1100 for updating an auto-exposure parameter at operation 514. As shown, the frame auto-exposure target and frame auto-exposure value are determined previously and used as inputs for operations shown in FIG. 11. For example, an operation 1102 may receive the frame auto-exposure value and frame auto-exposure target as inputs and may use them as a basis for determining a frame auto-exposure gain. The frame auto-exposure gain may be determined to correspond to a ratio of the frame auto-exposure target to the frame auto-exposure value. In this way, if the frame auto-exposure value is already equal to the frame auto-exposure target (e.g., such that no further adjustment is needed to align to the target), the frame auto-exposure gain may be set to a gain of 1, so that the system will neither try to boost nor attenuate the auto-exposure values for a subsequent frame that the image capture system captures. Conversely, if the frame auto-exposure target is different from the frame auto-exposure value, the frame auto-exposure gain may be set to correspond to a value less than or greater than 1 to cause the system to either boost or attenuate the auto-exposure values for the subsequent frame in an attempt to make the auto-exposure values more closely match the desired auto-exposure target.

At operation 1104, the frame auto-exposure gain may be taken as an input along with other data (e.g., other frame auto-exposure gains) determined for previous image frames in the image frame sequence. Based on these inputs, operation 1104 applies filtering to ensure that the auto-exposure gain does not change more quickly than desired and to thereby ensure that image frames presented to the user maintain a consistent brightness and change gradually (e.g., by not changing faster than a threshold rate). The filtering performed at operation 1104 may be performed using a smoothing filter such as a temporal infinite impulse response (IIR) filter or another such digital or analog filter as may serve a particular implementation.

At operation 1106, the filtered auto-exposure gain may be used as a basis for adjusting one or more auto-exposure parameters of the image capture system (e.g., for use by the image capture device or the illumination source in capturing additional image frames). For example, as described above, adjusted auto-exposure parameters may include an exposure time parameter, a shutter aperture parameter, a luminance gain parameter, or the like. For image capture systems in which the illumination of the scene is largely or completely controlled by the image capture system (e.g., an image capture system including an endoscopic image capture device described above; an image capture system including a flash or other illumination source, etc.), adjusted auto-exposure parameters may further include an illumination intensity parameter, an illumination duration parameter, or the like.

Adjustments to the auto-exposure parameters of the image capture system may cause the image capture system to expose subsequent image frames in various different ways. For example, by adjusting the exposure time parameter, a shutter speed may be adjusted for a shutter included in the image capture system. For instance, the shutter may be held open for a longer period of time (e.g., to thereby increase the amount of exposure time of an image sensor) or for a shorter period of time (e.g., to thereby decrease the amount of exposure time for the image sensor). As another example, by adjusting the shutter aperture parameter, an aperture of the shutter may be adjusted to open more widely (e.g., to thereby increase the amount of light exposed to the image sensor) or less widely (e.g., to thereby decrease the amount of light exposed to the image sensor). As yet another example, by adjusting the luminance gain parameter, a sensitivity (e.g., an ISO sensitivity) may be increased or decreased to amplify or attenuate the illuminance as captured by the image capture system. For implementations in which the image capture system controls the illumination of the scene, the illumination intensity and/or illumination duration parameters may be adjusted to increase the intensity and duration of the light used to illuminate the scene being captured, thereby also affecting how much light the image sensor is exposed to.

Returning to FIG. 5, after the operations of flow diagram 500 have been performed, the current image frame may be considered fully processed by apparatus 100 and flow may return to operation 502, where a subsequent image frame of the image frame sequence may be obtained. The process may be repeated for the subsequent image frame and/or other subsequent image frames. It will be understood that, in certain examples, every image frame may be analyzed in accordance with flow diagram 500 to keep the auto-exposure data points (e.g., frame auto-exposure value and frame auto-exposure target, etc.), and auto-exposure parameters as up-to-date as possible. In other examples, only certain image frames (e.g., every other image frame, every third image frame, etc.) may be so analyzed to conserve processing bandwidth in scenarios where more periodic auto-exposure processing still allows design specifications and targets to be achieved. It will also be understood that auto-exposure effects may tend to lag a few frames behind luminance changes at a scene, since auto-exposure parameter adjustments made based on one particular frame do not affect the exposure of that frame; but rather affect subsequent frames.

Based on any adjustments apparatus 100 makes to the auto-exposure parameters (and/or based on maintaining the auto-exposure parameters at their current levels when appropriate), apparatus 100 may successfully manage auto-exposure for image frames being captured by the image capture system; and subsequent image frames may be captured with desirable auto-exposure properties so as to have an attractive and beneficial appearance when presented to users.

As has been described, apparatus 100, method 200, and/or system 300 may each be associated in certain examples with a computer-assisted medical system used to perform a medical procedure (e.g., a surgical procedure, a diagnostic procedure, an exploratory procedure, etc.) on a body. To illustrate, FIG. 12 shows an illustrative computer-assisted medical system 1200 that may be used to perform various types of medical procedures including surgical and/or non-surgical procedures.

Figure 12:
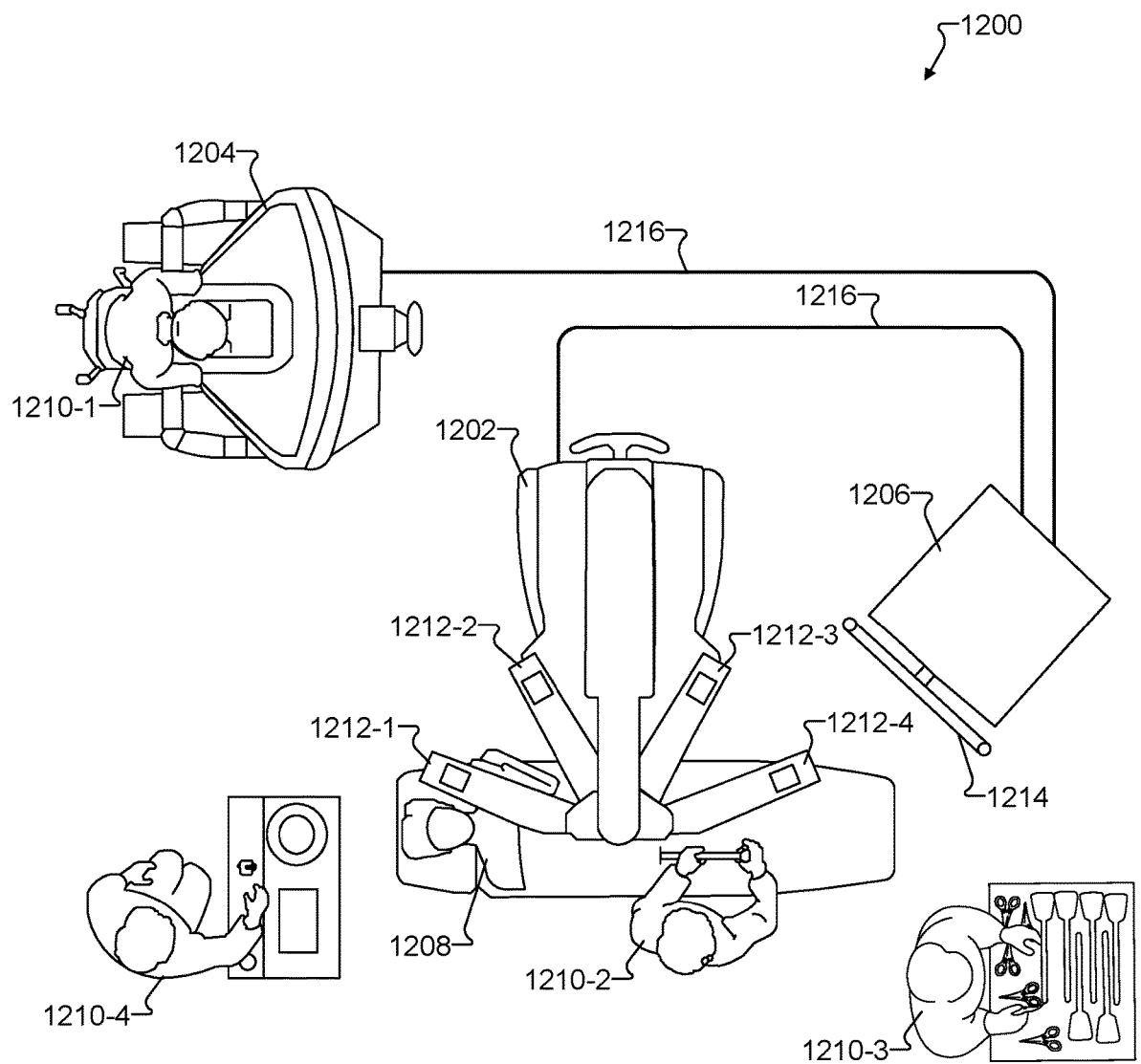
FIG. 12 shows an illustrative computer-assisted medical system according to principles described herein.

As shown, computer-assisted medical system 1200 may include a manipulator assembly 1202 (a manipulator cart is shown in FIG. 12), a user control apparatus 1204, and an auxiliary apparatus 1206, all of which are communicatively coupled to each other. Computer-assisted medical system 1200 may be utilized by a medical team to perform a computer-assisted medical procedure or other similar operation on a body of a patient 1208 or on any other body as may serve a particular implementation. As shown, the medical team may include a first user 1210-1 (such as a surgeon for a surgical procedure), a second user 1210-2 (such as a patient-side assistant), a third user 1210-3 (such as another assistant, a nurse, a trainee, etc.), and a fourth user 1210-4 (such as an anesthesiologist for a surgical procedure), all of whom may be collectively referred to as users 1210, and each of whom may control, interact with, or otherwise be a user of computer-assisted medical system 1200. More, fewer, or alternative users may be present during a medical procedure as may serve a particular implementation. For example, team composition for different medical procedures, or for non-medical procedures, may differ and include users with different roles.

While FIG. 12 illustrates an ongoing minimally invasive medical procedure such as a minimally invasive surgical procedure, it will be understood that computer-assisted medical system 1200 may similarly be used to perform open medical procedures or other types of operations. For example, operations such as exploratory imaging operations, mock medical procedures used for training purposes, and/or other operations may also be performed.

As shown in FIG. 12, manipulator assembly 1202 may include one or more manipulator arms 1212 (e.g., manipulator arms 1212-1 through 1212-4) to which one or more instruments may be coupled. The instruments may be used for a computer-assisted medical procedure on patient 1208 (e.g., in a surgical example, by being at least partially inserted into patient 1208 and manipulated within patient 1208). While manipulator assembly 1202 is depicted and described herein as including four manipulator arms 1212, it will be recognized that manipulator assembly 1202 may include a single manipulator arm 1212 or any other number of manipulator arms as may serve a particular implementation. While the example of FIG. 12 illustrates manipulator arms 1212 as being robotic manipulator arms, it will be understood that, in some examples, one or more instruments may be partially or entirely manually controlled, such as by being handheld and controlled manually by a person. For instance, these partially or entirely manually controlled instruments may be used in conjunction with, or as an alternative to, computer-assisted instrumentation that is coupled to manipulator arms 1212 shown in FIG. 12.

During the medical operation, user control apparatus 1204 may be configured to facilitate teleoperational control by user 1210-1 of manipulator arms 1212 and instruments attached to manipulator arms 1212. To this end, user control apparatus 1204 may provide user 1210-1 with imagery of an operational area associated with patient 1208 as captured by an imaging device. To facilitate control of instruments, user control apparatus 1204 may include a set of master controls. These master controls may be manipulated by user 1210-1 to control movement of the manipulator arms 1212 or any instruments coupled to manipulator arms 1212.

Auxiliary apparatus 1206 may include one or more computing devices configured to perform auxiliary functions in support of the medical procedure, such as providing insufflation, electrocautery energy, illumination or other energy for imaging devices, image processing, or coordinating components of computer-assisted medical system 1200. In some examples, auxiliary apparatus 1206 may be configured with a display monitor 1214 configured to display one or more user interfaces, or graphical or textual information in support of the medical procedure. In some instances, display monitor 1214 may be implemented by a touchscreen display and provide user input functionality.

As will be described in more detail below, apparatus 100 may be implemented within or may operate in conjunction with computer-assisted medical system 1200. For instance, in certain implementations, apparatus 100 may be implemented by computing resources included within an instrument (e.g., an endoscopic or other imaging instrument) attached to one of manipulator arms 1212, or by computing resources associated with manipulator assembly 1202, user control apparatus 1204, auxiliary apparatus 1206, or another system component not explicitly shown in FIG. 12.

Manipulator assembly 1202, user control apparatus 1204, and auxiliary apparatus 1206 may be communicatively coupled one to another in any suitable manner. For example, as shown in FIG. 12, manipulator assembly 1202, user control apparatus 1204, and auxiliary apparatus 1206 may be communicatively coupled by way of control lines 1216, which may represent any wired or wireless communication link as may serve a particular implementation. To this end, manipulator assembly 1202, user control apparatus 1204, and auxiliary apparatus 1206 may each include one or more wired or wireless communication interfaces, such as one or more local area network interfaces, Wi-Fi network interfaces, cellular interfaces, and so forth.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory (DRAM), which typically constitutes a main memory. Common forms of computer-readable media include, for example, a disk, hard disk, magnetic tape, any other magnetic medium, a compact disc read-only memory (CD-ROM), a digital video disc (DVD), any other optical medium, random access memory (RAM), programmable read-only memory (PROM), electrically erasable programmable read-only memory (EPROM), FLASH-EEPROM, any other memory chip or cartridge, or any other tangible medium from which a computer can read.

Figure 13:
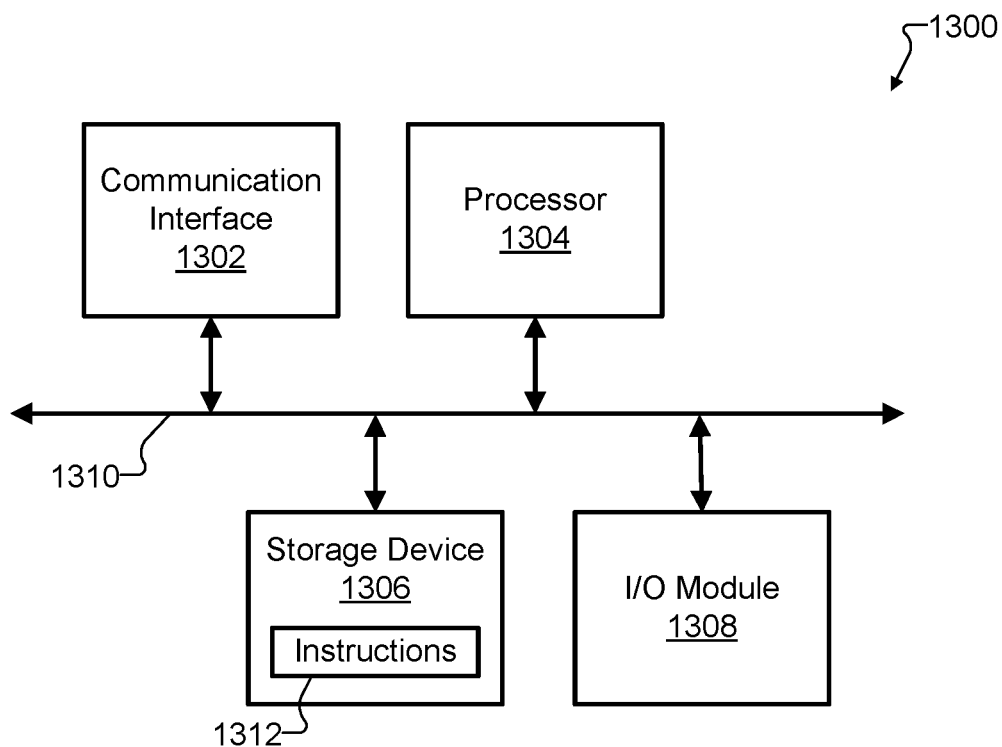
FIG. 13 shows an illustrative computing system according to principles described herein.

FIG. 13 shows an illustrative computing system 1300 that may be specifically configured to perform one or more of the processes described herein. For example, computing system 1300 may include or implement (or partially implement) an auto-exposure management apparatus such as apparatus 100, an auto-exposure management system such as system 300, or any other computing systems or devices described herein.

As shown in FIG. 13, computing system 1300 may include a communication interface 1302, a processor 1304, a storage device 1306, and an input/output ("I/O") module 1308 communicatively connected via a communication infrastructure 1310, While an illustrative computing system 1300 is shown in FIG. 13, the components illustrated in FIG. 13 are not intended to be limiting. Additional or alternative components may be used in other embodiments. Components of computing system 1300 shown in FIG. 13 will now be described in additional detail.

Communication interface 1302 may be configured to communicate with one or more computing devices. Examples of communication interface 1302 include, without limitation, a wired network interface (such as a network interface card), a wireless network interface (such as a wireless network interface card), a modem, an audio/video connection, and any other suitable interface.

Processor 1304 generally represents any type or form of processing unit capable of processing data or interpreting, executing, and/or directing execution of one or more of the instructions, processes, and/or operations described herein. Processor 1304 may direct execution of operations in accordance with one or more applications 1312 or other computer-executable instructions such as may be stored in storage device 1306 or another computer-readable medium.

Storage device 1306 may include one or more data storage media, devices, or configurations and may employ any type, form, and combination of data storage media and/or device. For example, storage device 1306 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1306. For example, data representative of one or more executable applications 1312 configured to direct processor 1304 to perform any of the operations described herein may be stored within storage device 1306. In some examples, data may be arranged in one or more databases residing within storage device 1306.

I/O module 1308 may include one or more I/O modules configured to receive user input and provide user output. One or more I/O modules may be used to receive input for a single virtual experience. I/O module 1308 may include any hardware, firmware, software, or combination thereof supportive of input and output capabilities. For example, I/O module 1308 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1308 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing system 1300. For example, one or more applications 1312 residing within storage device 1306 may be configured to direct processor 1304 to perform one or more processes or functions associated with processor 104 of apparatus 100. Likewise, memory 102 of apparatus 100 may be implemented by or within storage device 1306.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An apparatus comprising:
one or more hardware processors; and
memory storing executable instructions that, when executed by the one or more processors, cause the apparatus to:
determine a color-skew metric for an image frame captured by an image capture system, the color-skew metric quantifying how much the image frame is skewed to a particular color;
determine, based on the color-skew metric and an adaptive target control function, a frame auto-exposure target; and
update, based on the frame auto-exposure target, one or more of an exposure time parameter, a shutter aperture parameter, or an illumination intensity parameter for use by the image capture system to capture an additional image frame,
wherein the determining the color-skew metric for the image frame includes:
determining pixel color-skew metrics for a plurality of pixels included in the image frame, the pixel color-skew metrics indicative of an extent to which the plurality of pixels skew to the particular color; and
determining, based on the pixel color-skew metrics and weight values associated with the plurality of pixels, the color-skew metric for the image frame.

2. The apparatus of claim 1, wherein the determining the color-skew metric for the image frame includes:
normalizing color data representative of the image frame;
decomposing the color data to distinguish a chrominance property of the color data from a luminance property of the color data;
determining an extent to which the chrominance property of the color data skews to the particular color; and
based on the determining the extent to which the chrominance property of the color data skews to the particular color, determining the color-skew metric.

3. The apparatus of claim 1, wherein the determining the color-skew metric for the image frame further includes:
assigning, based on spatial positions of the plurality of pixels within the image frame, the weight values to the plurality of pixels within the image frame; and
determining, based on the pixel color-skew metrics and the assigned weight values, the color-skew metric for the image frame as a weighted average of the pixel color-skew metrics.

4. The apparatus of claim 1, wherein the determining the frame auto-exposure target includes:
determining a raw frame auto-exposure target based on the image frame captured by the image capture system;
determining a scaling value as an output of the adaptive target control function given an input of the color-skew metric; and
determining the frame auto-exposure target by scaling the raw frame auto-exposure target by the scaling value.

5. The apparatus of claim 4, wherein:
the color-skew metric given as the input does not exceed a color-skew threshold;
the output of the adaptive target control function comprises a null scaling value; and
the determining the frame auto-exposure target includes determining the frame auto-exposure target to equal the raw frame auto-exposure target.

6. The apparatus of claim 4, wherein:
the color-skew metric given as the input exceeds a color-skew threshold;
the output of the adaptive target control function comprises a reductive scaling value; and
the determining the frame auto-exposure target includes determining the frame auto-exposure target to equal the raw frame auto-exposure target reduced based on the reductive scaling value.

7. The apparatus of claim 4, wherein the determining the color-skew metric includes determining the color-skew metric to correspond to a value selected from a set of discrete values that each correspond to a different scaling value output by the adaptive target control function.

8. The apparatus of claim 1, wherein:
the image capture system includes an endoscopic image capture device configured to capture the image frame as part of an image frame sequence captured during a performance of a medical procedure on a body;
the image frame depicts an internal view of the body; and
the particular color comprises a red color.

9. The apparatus of claim 1, wherein:
the instructions, when executed by the one or more processors, cause the apparatus to:

determine a frame auto-exposure value of the image frame; and determine, based on the frame auto-exposure value and the frame auto-exposure target, a frame auto-exposure gain; and the updating the one or more of the exposure time parameter, the shutter aperture parameter, or the illumination intensity parameter is based on the frame auto-exposure gain.

10. The apparatus of claim 1, wherein the instructions, when executed by the one or more processors, cause the apparatus to update, based on the frame auto-exposure target, a luminance gain parameter.

11. A non-transitory computer-readable medium storing instructions that, when executed, cause one or more processors of a computing device to:

determine a color-skew metric for an image frame captured by an image capture system, the color-skew metric quantifying how much the image frame is skewed to a particular color;

determine an output of an adaptive target control function given an input of the color-skew metric; and update, based on the output of the adaptive target control function, one or more of an exposure time parameter, a shutter aperture parameter, or an illumination intensity parameter for use by the image capture system to capture an additional image frame, wherein the determining the color-skew metric for the image frame includes:

determining pixel color-skew metrics for a plurality of pixels included in the image frame, the pixel color-skew metrics indicative of an extent to which the plurality of pixels skew to the particular color; and determining, based on the pixel color-skew metrics and weight values associated with the plurality of pixels, the color-skew metric for the image frame.

12. The non-transitory computer-readable medium of claim 11, wherein the determining the color-skew metric for the image frame includes:

normalizing color data representative of the image frame;

decomposing the color data to distinguish a chrominance property of the color data from a luminance property of the color data;

determining an extent to which the chrominance property of the color data skews to the particular color; and based on the determining the extent to which the chrominance property of the color data skews to the particular color, determining the color-skew metric.

13. The non-transitory computer-readable medium of claim 11, wherein the determining the color-skew metric for the image frame further includes:

assigning, based on spatial positions of the plurality of pixels within the image frame, the weight values to the plurality of pixels within the image frame; and determining, based on the pixel color-skew metrics and the assigned weight values, the color-skew metric for the image frame as a weighted average of the pixel color-skew metrics.

14. The non-transitory computer-readable medium of claim 11, wherein the instructions, when executed, cause the one or more processors to:

determine, based on the image frame captured by the image capture system, a raw frame auto-exposure target; and determine a frame auto-exposure target by scaling the raw frame auto-exposure target by the output of the adaptive target control function given the input of the color-skew metric.

15. A method comprising:

determining, by a computing device, a color-skew metric for an image frame captured by an image capture system, the color-skew metric quantifying how much the image frame is skewed to a particular color;

determining, by the computing device and based on the color-skew metric, a frame auto-exposure target;

determining, by the computing device, a frame auto-exposure value; and updating, by the computing device and based on the frame auto-exposure target and the frame auto-exposure value, one or more of an exposure time parameter, a shutter aperture parameter, or an illumination intensity parameter for use by the image capture system to capture an additional image frame, wherein the determining the color-skew metric for the image frame includes:

determining pixel color-skew metrics for a plurality of pixels included in the image frame, the pixel color-skew metrics indicative of an extent to which the plurality of pixels skew to the particular color; and determining, based on the pixel color-skew metrics and weight values associated with the plurality of pixels, the color-skew metric for the image frame.

16. The method of claim 15, wherein the determining the color-skew metric for the image frame includes:

normalizing color data representative of the image frame;

decomposing the color data to distinguish a chrominance property of the color data from a luminance property of the color data;

determining an extent to which the chrominance property of the color data skews to the particular color; and based on the determining the extent to which the chrominance property of the color data skews to the particular color, determining the color-skew metric.

17. The method of claim 15, wherein the determining the color-skew metric for the image frame further includes:

assigning, based on spatial positions of the plurality of pixels within the image frame, the weight values to the plurality of pixels within the image frame determining, based on the pixel color-skew metrics and the assigned weight values, the color-skew metric for the image frame as a weighted average of the pixel color-skew metrics.

18. The method of claim 15, wherein the determining the frame auto-exposure target includes:

determining a raw frame auto-exposure target based on the image frame captured by the image capture system;

determining a scaling value as an output of an adaptive target control function given an input of the color-skew metric; and determining the frame auto-exposure target by scaling the raw frame auto-exposure target by the scaling value.

19. The method of claim 15, wherein:

the image capture system includes an endoscopic image capture device configured to capture the image frame as part of an image frame sequence captured during a performance of a medical procedure on a body;

the image frame depicts an internal view of the body; and the particular color comprises a red color.

20. The method of claim 15, further comprising determining, by the computing device based on the frame auto-exposure value and the frame auto-exposure target, a frame auto-exposure gain;
    wherein the updating the one or more of the exposure time parameter, the shutter aperture parameter, or the illumination intensity parameter is based on the frame auto-exposure gain.

\* \* \* \* \*